United States Patent
Yoshida et al.

(10) Patent No.: US 12,089,589 B2
(45) Date of Patent: *Sep. 17, 2024

(54) IRRADIATION OF RED BLOOD CELLS AND ANAEROBIC STORAGE

(71) Applicant: Hemanext Inc., Lexington, MA (US)

(72) Inventors: Tatsuro Yoshida, West Newton, MA (US); Paul Vernucci, Billerica, MA (US)

(73) Assignee: Hemanext Inc., Lexington, MA (US)

( * ) Notice: Subject to any disclaimer, the term of this patent is extended or adjusted under 35 U.S.C. 154(b) by 219 days.

This patent is subject to a terminal disclaimer.

(21) Appl. No.: 17/702,586

(22) Filed: Mar. 23, 2022

(65) Prior Publication Data

US 2022/0211030 A1    Jul. 7, 2022

Related U.S. Application Data

(63) Continuation of application No. 16/156,136, filed on Oct. 10, 2018, now Pat. No. 11,284,616, which is a continuation of application No. 13/289,722, filed on Nov. 4, 2011, now Pat. No. 10,136,635, which is a continuation-in-part of application No. 12/901,350, filed on Oct. 8, 2010, now Pat. No. 8,535,421.

(60) Provisional application No. 61/410,684, filed on Nov. 5, 2010, provisional application No. 61/331,693, filed on May 5, 2010, provisional application No. 61/250,661, filed on Oct. 12, 2009.

(51) Int. Cl.
| | |
|---|---|
| *A01N 1/02* | (2006.01) |
| *A61K 35/18* | (2015.01) |
| *A61J 1/10* | (2006.01) |
| *A61L 2/08* | (2006.01) |

(52) U.S. Cl.
CPC ......... *A01N 1/0242* (2013.01); *A01N 1/0205* (2013.01); *A01N 1/0263* (2013.01); *A01N 1/0278* (2013.01); *A01N 1/0294* (2013.01); *A61K 35/18* (2013.01); *A61J 1/10* (2013.01); *A61L 2/081* (2013.01); *A61L 2/082* (2013.01); *A61L 2202/181* (2013.01); *A61L 2202/22* (2013.01)

(58) Field of Classification Search
CPC .... A01N 1/0242; A01N 1/0205; A61K 35/18; A61L 2202/22
See application file for complete search history.

(56) References Cited

U.S. PATENT DOCUMENTS

| | | |
|---|---|---|
| 3,064,647 A | 11/1962 | Earl |
| 3,361,041 A | 1/1968 | Grob |
| 3,489,647 A | 1/1970 | Kolobow |
| 3,668,837 A | 6/1972 | Gross |
| 3,668,838 A | 6/1972 | McNeil et al. |
| 3,803,810 A | 4/1974 | Rosenberg |
| 3,910,841 A | 10/1975 | Esmond |
| 3,942,529 A | 3/1976 | Waage |
| 4,075,091 A | 2/1978 | Bellhouse |
| 4,086,924 A | 5/1978 | Latham, Jr. |
| 4,093,515 A | 6/1978 | Kolobow |
| 4,131,200 A | 12/1978 | Rinfret |
| 4,162,676 A | 7/1979 | Talcott |
| 4,199,062 A | 4/1980 | Johnston et al. |
| 4,222,379 A | 9/1980 | Smith |
| 4,225,439 A | 9/1980 | Spranger |
| 4,228,032 A | 10/1980 | Talcott |
| 4,253,458 A | 3/1981 | Bacehowski et al. |
| 4,256,692 A | 3/1981 | Cover |
| 4,262,581 A | 4/1981 | Ferrell |
| 4,300,559 A | 11/1981 | Gajewski et al. |
| 4,314,480 A | 2/1982 | Becker |
| 4,342,723 A | 8/1982 | Sado et al. |
| 4,366,179 A | 12/1982 | Nawata et al. |
| 4,370,160 A | 1/1983 | Ziemelis |
| 4,381,775 A | 5/1983 | Nose' et al. |
| 4,386,069 A | 5/1983 | Estep |
| 4,398,642 A | 8/1983 | Okudaira et al. |
| 4,440,815 A | 4/1984 | Zomorodi et al. |
| 4,455,299 A | 6/1984 | Grode |
| 4,540,416 A | 9/1985 | Hattori et al. |
| 4,568,328 A | 2/1986 | King et al. |
| 4,572,899 A | 2/1986 | Walker et al. |
| 4,579,223 A | 4/1986 | Otsuka et al. |
| 4,585,735 A | 4/1986 | Meryman et al. |
| 4,609,383 A | 9/1986 | Bonaventura et al. |

(Continued)

FOREIGN PATENT DOCUMENTS

| | | |
|---|---|---|
| AU | 2012279043 | 7/2016 |
| CA | 2477946 | 9/2003 |

(Continued)

OTHER PUBLICATIONS

Extended European Search Report dated Jun. 16, 2023 in European Patent Application No. 23162955.1.

(Continued)

*Primary Examiner* — Taeyoon Kim

(74) *Attorney, Agent, or Firm* — Arnold & Porter Kaye Scholer

(57) ABSTRACT

A blood storage system comprising: a collection vessel for red blood cells; an oxygen or oxygen and carbon dioxide depletion device; a storage vessel for red blood cells; tubing connecting the collection vessel to the oxygen or oxygen and carbon dioxide depletion device and the oxygen or oxygen and carbon dioxide depletion device to the storage vessel; and a gamma or X-ray irradiating device is used to irradiate red blood cells stored in the vessel, storing red blood cells under anaerobic conditions.

18 Claims, 17 Drawing Sheets

(56) References Cited

U.S. PATENT DOCUMENTS

| | | |
|---|---|---|
| 4,629,544 A | 12/1986 | Bonaventura et al. |
| 4,639,353 A | 1/1987 | Takemura et al. |
| 4,654,053 A | 3/1987 | Sievers et al. |
| 4,659,549 A | 4/1987 | Hamada et al. |
| 4,670,013 A | 6/1987 | Barnes et al. |
| 4,701,267 A | 10/1987 | Watanabe et al. |
| 4,713,176 A | 12/1987 | Schoendorfer et al. |
| 4,731,978 A | 5/1988 | Martensson |
| 4,748,121 A | 5/1988 | Beaver et al. |
| 4,749,551 A | 6/1988 | Borgione |
| 4,769,175 A | 9/1988 | Inoue |
| 4,769,318 A | 9/1988 | Hamasaki et al. |
| 4,798,728 A | 1/1989 | Sugisawa |
| 4,828,561 A | 5/1989 | Woodroof |
| 4,837,047 A | 6/1989 | Sato et al. |
| 4,859,360 A | 8/1989 | Suzuki et al. |
| 4,861,867 A | 8/1989 | Estep |
| 4,880,548 A | 11/1989 | Pall et al. |
| 4,880,786 A | 11/1989 | Sasakawa et al. |
| 4,902,701 A | 2/1990 | Batchelor et al. |
| 4,925,572 A | 5/1990 | Pall |
| 4,986,837 A | 1/1991 | Shibata |
| 4,998,990 A | 3/1991 | Richter et al. |
| 5,000,848 A | 3/1991 | Hodgins et al. |
| 5,023,054 A | 6/1991 | Sato et al. |
| 5,037,419 A | 8/1991 | Valentine et al. |
| 5,120,659 A | 6/1992 | King et al. |
| 5,137,531 A | 8/1992 | Lee et al. |
| 5,139,668 A | 8/1992 | Pan et al. |
| 5,143,763 A | 9/1992 | Yamada et al. |
| 5,152,905 A | 10/1992 | Pall et al. |
| 5,192,320 A | 3/1993 | Anazawa et al. |
| 5,194,158 A | 3/1993 | Matson |
| 5,208,335 A | 5/1993 | Ramprasad et al. |
| 5,229,012 A | 7/1993 | Pall et al. |
| 5,254,248 A | 10/1993 | Nakamura et al. |
| 5,286,407 A | 2/1994 | Inoue et al. |
| 5,328,268 A | 7/1994 | LaFleur |
| 5,353,793 A | 10/1994 | Bornn |
| 5,356,375 A | 10/1994 | Higley |
| 5,360,734 A | 11/1994 | Chapman et al. |
| 5,362,442 A | 11/1994 | Kent |
| 5,368,808 A | 11/1994 | Koike et al. |
| 5,382,526 A | 1/1995 | Gajewski et al. |
| 5,386,014 A | 1/1995 | Nho et al. |
| 5,387,624 A | 2/1995 | Morita et al. |
| 5,417,986 A | 5/1995 | Reid et al. |
| 5,427,663 A | 6/1995 | Austin et al. |
| 5,443,743 A | 8/1995 | Gsell |
| 5,449,617 A | 9/1995 | Falkenberg et al. |
| 5,476,764 A | 12/1995 | Bitensky |
| 5,506,141 A | 4/1996 | Weinreb et al. |
| 5,529,821 A | 6/1996 | Ishikawa et al. |
| 5,605,934 A | 2/1997 | Giertych |
| 5,617,873 A | 4/1997 | Yost et al. |
| 5,624,794 A | 4/1997 | Bitensky et al. |
| 5,635,358 A | 6/1997 | Wilding et al. |
| 5,686,304 A | 11/1997 | Codner |
| 5,691,452 A | 11/1997 | Gawryl et al. |
| 5,693,122 A | 12/1997 | Berndt |
| 5,693,230 A | 12/1997 | Asher |
| 5,698,250 A | 12/1997 | DelDuca et al. |
| 5,709,472 A | 1/1998 | Prusik et al. |
| 5,744,056 A | 4/1998 | Venkateshwaran et al. |
| 5,730,989 A | 5/1998 | Wright |
| 5,750,115 A | 5/1998 | Van Den Bosch |
| 5,783,094 A | 7/1998 | Kraus et al. |
| 5,783,148 A | 7/1998 | Cottingham et al. |
| 5,789,151 A | 8/1998 | Bitensky et al. |
| 5,789,152 A | 8/1998 | Black et al. |
| 5,811,142 A | 9/1998 | DelDuca et al. |
| 5,846,427 A | 12/1998 | Kessler et al. |
| 5,858,015 A | 1/1999 | Fini |
| 5,858,643 A | 1/1999 | Ben-Hur et al. |
| 5,863,460 A | 1/1999 | Slovacek et al. |
| 5,895,810 A | 4/1999 | Light et al. |
| 5,902,747 A | 5/1999 | Nemser et al. |
| 5,906,285 A | 5/1999 | Slat |
| 5,928,178 A | 7/1999 | Samolyk |
| 5,955,519 A | 9/1999 | Neri |
| 5,962,650 A | 10/1999 | Osterberg et al. |
| 5,972,710 A | 10/1999 | Weigl et al. |
| 6,007,529 A | 12/1999 | Gustafsson et al. |
| 6,027,623 A | 2/2000 | Ohkawa |
| 6,042,264 A | 3/2000 | Prusik et al. |
| 6,045,701 A | 4/2000 | Ung-Chhun et al. |
| 6,047,203 A | 4/2000 | Sackner et al. |
| 6,068,152 A | 5/2000 | Meiners et al. |
| 6,076,664 A | 6/2000 | Yeager |
| 6,080,322 A | 6/2000 | Deniega et al. |
| 6,090,062 A | 7/2000 | Sood et al. |
| 6,097,293 A | 8/2000 | Galloway et al. |
| 6,148,536 A | 11/2000 | Iijima |
| 6,150,085 A | 11/2000 | Hess et al. |
| 6,156,231 A | 12/2000 | McKedy |
| 6,162,396 A | 12/2000 | Bitensky et al. |
| 6,164,821 A | 12/2000 | Randall |
| 6,187,572 B1 | 2/2001 | Platz et al. |
| 6,210,601 B1 | 4/2001 | Hottle et al. |
| 6,231,770 B1 | 5/2001 | Bormann et al. |
| 6,248,690 B1 | 6/2001 | McKedy |
| 6,254,628 B1 | 7/2001 | Wallace et al. |
| 6,287,284 B1 | 9/2001 | Woarburton-Pitt |
| 6,287,289 B1 | 9/2001 | Niedospial, Jr. |
| 6,315,815 B1 | 11/2001 | Spadaccini |
| 6,337,026 B1 | 1/2002 | Lee et al. |
| 6,358,678 B1 | 3/2002 | Bakaltcheva et al. |
| 6,368,871 B1 | 4/2002 | Christel et al. |
| 6,387,461 B1 | 5/2002 | Ebner et al. |
| 6,402,818 B1 | 6/2002 | Sengupta et al. |
| 6,403,124 B1 | 6/2002 | Dottori |
| 6,413,713 B1 | 7/2002 | Serebrennikov |
| 6,436,872 B2 | 8/2002 | McKedy |
| 6,439,577 B2 | 8/2002 | Jorgensen et al. |
| 6,447,987 B1 | 9/2002 | Hess et al. |
| 6,468,732 B1 | 10/2002 | Malin et al. |
| 6,475,147 B1 | 11/2002 | Yost et al. |
| 6,479,252 B1 | 11/2002 | Barbera-Guillem et al. |
| 6,482,585 B2 | 11/2002 | Dottori |
| 6,494,909 B2 | 12/2002 | Greenhalgh |
| 6,527,957 B1 | 3/2003 | Denienga et al. |
| 6,558,571 B1 | 5/2003 | Powers |
| 6,564,207 B1 | 5/2003 | Abdoh |
| 6,582,496 B1 | 6/2003 | Cheng et al. |
| 6,610,772 B1 | 8/2003 | Clauberg et al. |
| 6,626,884 B1 | 9/2003 | Dillon et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |
| 6,709,492 B1 | 3/2004 | Spadaccini |
| 6,723,051 B2 | 4/2004 | Davidson et al. |
| 6,761,695 B2 | 7/2004 | Yost et al. |
| 6,773,407 B2 | 8/2004 | Yost et al. |
| 6,808,675 B1 | 10/2004 | Coelho et al. |
| 6,817,979 B2 | 11/2004 | Nihtilä |
| 6,866,783 B2 | 3/2005 | Baurmeister et al. |
| 6,878,335 B2 | 4/2005 | Britten et al. |
| 6,899,822 B2 | 5/2005 | McKedy |
| 6,955,648 B2 | 10/2005 | Mozayeni et al. |
| 6,977,105 B1 | 12/2005 | Fujieda et al. |
| 7,041,800 B1 | 5/2006 | Gawryl et al. |
| 7,097,690 B2 | 8/2006 | Usher et al. |
| 7,104,958 B2 | 9/2006 | Crutchfield et al. |
| 7,125,498 B2 | 10/2006 | McKedy |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |
| 7,452,601 B2 | 11/2008 | Ebner et al. |
| 7,517,146 B2 | 4/2009 | Smith et al. |
| 7,666,486 B2 | 2/2010 | Sato et al. |
| 7,713,614 B2 | 5/2010 | Chow et al. |
| 7,721,898 B2 | 5/2010 | Yagi et al. |
| 7,723,017 B2 | 5/2010 | Bitensky et al. |

(56) References Cited

U.S. PATENT DOCUMENTS

| | | |
|---|---|---|
| 7,754,798 B2 | 7/2010 | Ebner et al. |
| 7,763,097 B2 | 7/2010 | Federspiel |
| 7,775,376 B2 | 8/2010 | Bonaguidi et al. |
| 7,784,619 B2 | 8/2010 | Jacobson |
| 8,070,664 B2 | 12/2011 | Rochat |
| 8,071,282 B2 | 12/2011 | Bitensky et al. |
| 8,535,421 B2 | 9/2013 | Yoshida et al. |
| 8,569,052 B2 | 10/2013 | Federspiel et al. |
| 8,864,735 B2 | 10/2014 | Sano et al. |
| 8,877,508 B2 | 11/2014 | Hyde et al. |
| 8,887,721 B2 | 11/2014 | Zapol et al. |
| 9,005,343 B2 | 4/2015 | Yoshida et al. |
| 9,067,004 B2 | 6/2015 | Yoshida et al. |
| 9,199,016 B2 | 12/2015 | Yoshida et al. |
| 9,296,990 B2 | 3/2016 | Federspiel et al. |
| 9,539,375 B2 | 1/2017 | Yoshida et al. |
| 9,801,784 B2 | 10/2017 | Yoshida et al. |
| 9,844,615 B2 | 12/2017 | Yoshida et al. |
| 10,295,781 B2 | 5/2019 | Park et al. |
| 10,603,417 B2 | 3/2020 | Yoshida et al. |
| 2001/0027156 A1 | 10/2001 | Egozy et al. |
| 2001/0037078 A1 | 11/2001 | Lynn et al. |
| 2001/0049089 A1 | 12/2001 | Dottori |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0176798 A1 | 11/2002 | Linker et al. |
| 2002/0182241 A1 | 12/2002 | Borenstein et al. |
| 2003/0003575 A1 | 1/2003 | Vacanti et al. |
| 2003/0039582 A1 | 2/2003 | Chambers et al. |
| 2003/0040835 A1 | 2/2003 | Ng et al. |
| 2003/0062299 A1 | 4/2003 | Lee et al. |
| 2003/0106861 A1 | 6/2003 | Gibbs et al. |
| 2003/0124504 A1 | 7/2003 | Bitensky et al. |
| 2003/0153074 A1 | 8/2003 | Bitensky et al. |
| 2003/0183801 A1 | 10/2003 | Yang et al. |
| 2003/0189003 A1 | 10/2003 | Kraus et al. |
| 2003/0190272 A1 | 10/2003 | Raine et al. |
| 2003/0201160 A1 | 10/2003 | Goodrich et al. |
| 2003/0215784 A1 | 11/2003 | Dumont et al. |
| 2003/0233934 A1 | 12/2003 | Wijmans et al. |
| 2004/0013566 A1 | 1/2004 | Myrick et al. |
| 2004/0026341 A1 | 2/2004 | Hogberg et al. |
| 2004/0097862 A1 | 5/2004 | Lampeter et al. |
| 2004/0126880 A1 | 7/2004 | Manders et al. |
| 2004/0146671 A1 | 7/2004 | Szabo et al. |
| 2004/0168982 A1 | 9/2004 | Bitensky et al. |
| 2004/0254560 A1 | 12/2004 | Coelho et al. |
| 2005/0038342 A1 | 2/2005 | Mozayeni et al. |
| 2005/0085785 A1 | 4/2005 | Shang et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0210141 A1 | 9/2005 | Oyama et al. |
| 2005/0230856 A1 | 10/2005 | Parekh et al. |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2006/0160724 A1 | 7/2006 | Gawryl et al. |
| 2006/0169138 A1 | 8/2006 | Schmidt |
| 2006/0226087 A1 | 10/2006 | Robinson et al. |
| 2006/0278073 A1 | 12/2006 | McHugh |
| 2007/0078113 A1 | 4/2007 | Roth et al. |
| 2007/0099170 A1 | 5/2007 | Goodrich et al. |
| 2007/0207186 A1 | 9/2007 | Scanlon et al. |
| 2007/0240569 A1 | 10/2007 | Ooya |
| 2007/0276508 A1 | 11/2007 | Fischer et al. |
| 2008/0027368 A1 | 1/2008 | Kollar et al. |
| 2008/0098894 A1 | 5/2008 | Sabatino |
| 2008/0160107 A1 | 7/2008 | McCaney et al. |
| 2008/0234327 A1 | 9/2008 | Cadieux et al. |
| 2008/0243045 A1 | 10/2008 | Pasqualini |
| 2008/0276803 A1 | 11/2008 | Molaison et al. |
| 2008/0299538 A1 | 12/2008 | Goodrich et al. |
| 2009/0017128 A1 | 1/2009 | Monzyk et al. |
| 2009/0084720 A1 | 4/2009 | Dannenmaier et al. |
| 2009/0235619 A1 | 9/2009 | Ostler et al. |
| 2009/0269837 A1 | 10/2009 | Shevkoplyas et al. |
| 2010/0021879 A1 | 1/2010 | Delgado et al. |
| 2010/0133203 A1 | 6/2010 | Walker et al. |
| 2010/0221697 A1 | 9/2010 | Sehgal |
| 2010/0282662 A1 | 11/2010 | Lee et al. |
| 2010/0294128 A1 | 11/2010 | Schmidt |
| 2010/0313755 A1 | 12/2010 | Koros et al. |
| 2010/0331767 A1 | 12/2010 | Frankowski |
| 2011/0092875 A1 | 4/2011 | Beck |
| 2012/0024156 A1 | 2/2012 | Yoshida et al. |
| 2012/0077182 A1 | 3/2012 | Bitensky et al. |
| 2012/0100523 A1 | 4/2012 | Federspiel et al. |
| 2012/0115124 A1 | 5/2012 | Yoshida et al. |
| 2012/0129148 A1 | 5/2012 | Hess et al. |
| 2012/0129149 A1 | 5/2012 | Federspiel et al. |
| 2012/0146266 A1 | 6/2012 | Oda et al. |
| 2012/0219633 A1 | 8/2012 | Sowemimo-Coker |
| 2013/0004586 A1 | 1/2013 | Vachon et al. |
| 2013/0004937 A1 | 1/2013 | Yoshida et al. |
| 2013/0144266 A1 | 6/2013 | Borenstein et al. |
| 2013/0197420 A1 | 8/2013 | Fissell, IV et al. |
| 2013/0259744 A1 | 10/2013 | Yoshida et al. |
| 2013/0327677 A1 | 12/2013 | McDorman |
| 2014/0012185 A1 | 1/2014 | Ishizuka et al. |
| 2014/0134503 A1 | 5/2014 | Lockett et al. |
| 2014/0146266 A1 | 5/2014 | Zhang |
| 2014/0158604 A1 | 6/2014 | Chammas et al. |
| 2014/0248005 A1 | 9/2014 | David et al. |
| 2015/0306288 A1 | 10/2015 | Delorme et al. |
| 2016/0007588 A1 | 1/2016 | Levesque et al. |
| 2016/0242410 A9 | 8/2016 | Yoshida et al. |
| 2018/0087997 A1 | 3/2018 | Thenard et al. |
| 2018/0094269 A1 | 4/2018 | Miller et al. |
| 2019/0275152 A1 | 9/2019 | Sowemimo-Coker et al. |

FOREIGN PATENT DOCUMENTS

| | | |
|---|---|---|
| CN | 1195965 A | 10/1998 |
| CN | 2502700 Y | 7/2002 |
| CN | 1642628 A | 7/2005 |
| CN | 2780207 Y | 5/2006 |
| CN | 2894710 Y | 5/2007 |
| CN | 101039737 A | 9/2007 |
| CN | 102711865 A | 10/2012 |
| CN | 103732056 | 4/2014 |
| DE | 3722984 | 1/1989 |
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| EP | 0 890 368 A1 | 1/1999 |
| EP | 1 245 217 A2 | 10/2002 |
| EP | 1109447 | 10/2003 |
| EP | 1 891 999 A1 | 2/2008 |
| EP | 2389064 | 11/2011 |
| EP | 2635114 | 9/2013 |
| EP | 2459247 A2 | 3/2016 |
| EP | 3 285 711 A1 | 10/2016 |
| EP | 3 268 015 A1 | 1/2018 |
| FR | 2 581 289 A1 | 11/1986 |
| FR | 2 996 413 A1 | 4/2014 |
| GB | 1 044 649 A2 | 10/1966 |
| GB | 2283015 A1 | 4/1995 |
| JP | S57-3652 A | 1/1982 |
| JP | 58-194879 | 11/1983 |
| JP | 59-115349 | 7/1984 |
| JP | 61-109577 A | 5/1986 |
| JP | 63-63616 A | 3/1988 |
| JP | 01-013860 | 3/1989 |
| JP | 01-104271 A | 4/1989 |
| JP | 3-284263 | 12/1991 |
| JP | H 04-364850 | 12/1992 |
| JP | 5-503075 A | 5/1993 |
| JP | 5-503304 A | 6/1993 |
| JP | H05-148151 A | 6/1993 |

(56) References Cited

FOREIGN PATENT DOCUMENTS

| | | |
|---|---|---|
| JP | 5-305123 A | 11/1993 |
| JP | H05-317413 | 12/1993 |
| JP | 06-121920 A | 5/1994 |
| JP | 2668446 | 7/1997 |
| JP | 2700170 B2 | 1/1998 |
| JP | H 10-501443 A | 2/1998 |
| JP | H10-507395 | 7/1998 |
| JP | 11-216179 | 8/1999 |
| JP | 2000-516963 A | 12/2000 |
| JP | 2001-500053 | 1/2001 |
| JP | 2001-523225 | 11/2001 |
| JP | 2002-087971 | 3/2002 |
| JP | 2002-253936 A | 9/2002 |
| JP | 2002-541941 | 12/2002 |
| JP | 2003-010287 | 1/2003 |
| JP | 2004-089495 A | 3/2004 |
| JP | 2004-514680 | 5/2004 |
| JP | 2004-520448 | 7/2004 |
| JP | 2004-244044 | 9/2004 |
| JP | 2005-533041 A | 11/2005 |
| JP | 2005-535279 A | 11/2005 |
| JP | 2005-535289 A | 11/2005 |
| JP | 2006-502078 A | 1/2006 |
| JP | 2006-515279 | 5/2006 |
| JP | 2006-213923 | 8/2006 |
| JP | 2007-260393 A | 10/2007 |
| JP | 2008-86996 | 4/2008 |
| JP | 2008-518952 | 6/2008 |
| JP | 2008-528066 | 7/2008 |
| JP | 2008-529550 A | 8/2008 |
| JP | 2008-253452 | 10/2008 |
| JP | 2009-513235 | 4/2009 |
| JP | 10/501443 | 2/2010 |
| JP | 2010-503501 A | 2/2010 |
| JP | 2010-509353 | 3/2010 |
| JP | 2010-116626 | 5/2010 |
| JP | 2010-535235 | 11/2010 |
| JP | 2010-538735 | 12/2010 |
| JP | 2011 000132 A | 1/2011 |
| JP | 2011-92905 | 5/2011 |
| JP | 2011-516570 A | 5/2011 |
| JP | 2013-500794 | 1/2013 |
| JP | 2013-507226 | 3/2013 |
| JP | 2014-501501 | 1/2014 |
| JP | 2014-518283 | 7/2014 |
| JP | 2014-527436 | 10/2014 |
| JP | 2007-509206 A | 4/2017 |
| KR | 10-0721054 | 5/2006 |
| SU | 1718766 A1 | 1/1990 |
| WO | WO 1981/02239 A1 | 8/1981 |
| WO | WO 1986/00809 A1 | 2/1986 |
| WO | WO 1989/02274 A1 | 3/1989 |
| WO | WO 1991/04659 A1 | 4/1991 |
| WO | WO 1992/08348 A1 | 5/1992 |
| WO | WO 1995/29662 A2 | 11/1995 |
| WO | WO 1996/29103 A1 | 9/1996 |
| WO | WO 1996/29346 A1 | 9/1996 |
| WO | WO 1996/29864 A1 | 10/1996 |
| WO | WO 1996/39026 A1 | 12/1996 |
| WO | WO 1997/37628 A1 | 10/1997 |
| WO | WO 1998/046073 A1 | 10/1998 |
| WO | WO 1998/51147 A1 | 11/1998 |
| WO | WO 1999/25726 A1 | 5/1999 |
| WO | WO 1999/29346 A1 | 6/1999 |
| WO | WO 1999/36330 A1 | 7/1999 |
| WO | WO 1999/48963 A2 | 9/1999 |
| WO | WO 2000/011946 A2 | 3/2000 |
| WO | WO 2000/0062891 | 10/2000 |
| WO | WO 01/10470 A1 | 2/2001 |
| WO | WO 2002/043485 | 6/2002 |
| WO | WO 2002/096471 | 12/2002 |
| WO | WO 2003/043419 A1 | 5/2003 |
| WO | WO 2003/043571 A2 | 5/2003 |
| WO | WO 2003/086577 A1 | 10/2003 |
| WO | WO 03/103390 A1 | 12/2003 |
| WO | WO 2003/103390 A1 | 12/2003 |
| WO | WO 2004/043381 A2 | 5/2004 |
| WO | WO 2006/050328 A1 | 5/2006 |
| WO | WO 2006/057473 A1 | 6/2006 |
| WO | WO 2006/088455 A1 | 8/2006 |
| WO | WO 2008/034476 A1 | 3/2008 |
| WO | WO 2008/063868 | 5/2008 |
| WO | WO 2009/126786 A2 | 10/2009 |
| WO | WO 2009/132839 A1 | 11/2009 |
| WO | WO 2011/014855 A2 | 2/2011 |
| WO | WO 2011/046841 A1 | 4/2011 |
| WO | WO 2011/046963 A1 | 4/2011 |
| WO | WO 2011/068897 A1 | 6/2011 |
| WO | WO 2012/027582 A1 | 3/2012 |
| WO | WO 2012/061731 A1 | 5/2012 |
| WO | WO 2012/120927 A1 | 9/2012 |
| WO | WO 2013/006631 A1 | 1/2013 |
| WO | WO 2013/022491 A1 | 2/2013 |
| WO | WO 2013/023156 A1 | 2/2013 |
| WO | WO 2013/043658 A1 | 3/2013 |
| WO | WO 2013/153441 A1 | 10/2013 |
| WO | WO 2013/177339 A1 | 11/2013 |
| WO | WO 2014/006238 | 1/2014 |
| WO | WO 2014/134503 A1 | 9/2014 |
| WO | WO 2014/194931 A1 | 12/2014 |
| WO | WO 2016/145210 A1 | 9/2016 |
| WO | WO 2016/172645 A1 | 10/2016 |
| WO | WO 2017/205590 A2 | 11/2017 |

OTHER PUBLICATIONS

Dupont, "What is Tyvek(R)," downloaded from www.dupont.com/what-is-tyvek.html, (2022).

"Oxygen O2 in Blood," downloaded from http://web.utk.edu/~rstrange/wfs550/index2.html (2022).

U.S. Appl. No. 62/131,130, filed Mar. 15, 2015, Wolf et al.

U.S. Appl. No. 62/151,957, filed Apr. 23, 2015, Yoshida et al.

U.S. Appl. No. 12/901,350, filed Oct. 8, 2010, Yoshida et al.

Agarwal et al., "Effect of pre-storage gamma irradiation on red blood cells," *Indian Journal of Medical Research* 122(5):385 (2005).

Alcantar et al., "Polyethylene glycol-coated biocompatible surfaces," *Journal of Biomedical Materials Research*, 51(3):343-351 (2000).

Anderson et al., "Microfabrication and microfluidics for tissue engineering: state of the art and future opportunities," *Lab Chip*, 4:98-103 (2004).

Apstein et al., "Effect of erythrocyte storage and oxyhemoglobin affinity changes on cardiac function," *Am J. Physiol* 248: H508-15 (1985).

Aydogan et al., "Impaired erythrocytes deformability in $H(2)O(2)$-induced oxidative stress: protective effect of L-carnosine," *Clin Hemorheol Microcirc* 39: 93-8 (2008).

Babic, "In vitro function and phagocytosis of galactosylated platelet concentrates after longterm refrigeration," *Transfusion* 47: 442-51 (2007).

Barbee et al., "The Fahraeus Effect," *Microvascular Research*, 3:6-16 (1971).

Barclay et al., "A Method for Detecting Chaos in Canine Myocardial Microcirculatory Red Cell Flux," *Microcirculation*, 7(5):335-346 (2000).

Bardy et al., "Technetium-99m Labeling by Means of Stannous Pyrophosphate: Application to Bleomycin and Red Blood Cells," *Journal of Nuclear Medicine*, 16(5):435-437 (1975).

Barras et al., "Influence of Rejuvenation on the Rheological Properties of Stored Erythrocytes," *VASA*, 23(4):305-311 (1994).

Basu et al., "Overview of blood components and their preparation," *Indian J Anaesth* 58:529-537 (2014).

Becker et al., "Studies of platelet concentrates stored at 22 C nad 4 C," *Transfusion* 13: 61-8 (1973).

Benesch et al., "The effect of organic phosphates from the human erythrocyte on the allosteric properties of hemoglobin," *Biochem Biophys Res Commun* 26: 162-7 (1967).

Bensinger et al., "Prolonged maintenance of 2,3-DPG in liquid blood storage: Use of an internal $CO_2$ trap to stabilize pH," *J. Lab. Clin. Med.*, 89(3):498-503 (1977).

(56) References Cited

OTHER PUBLICATIONS

Benson et al., "Accumulation of Pro-Cancer Cytokines in the Plasma Fraction of Stored Packed Red Cells," *J Gastrointest Surg.*, 16:460-468 (2012).
Bersin et al., "Importance of oxygen-haemoglobin binding to oxygen transport in congestive heart failure," *Br Heart J* 70: 443-7 (1993).
Beutler et al., "Storage of red cell concentrates in CPD-A2 for 42 and 49 days," *The Journal of Laboratory and Clinical Medicine*, 102(1):53-62 (1983).
Bordbar et al., "Identified metabolic signature for assessing red blood cell unit quality is associated with endothelial damage markers and clinical outcomes," *Transfusion* 56: 852-62 (2016).
Borenstein et al., "Microfabrication Technology for Vascularized Tissue Engineering," *Biomedical Microdevices*, 4(3):167-175 (2002).
Brody et al., "Deformation and Flow of Red Blood Cells in a Synthetic Lattice: Evidence for an Active Cytoskeleton," *Biophysical Journal*, 68:2224-2232 (1995).
Browne et al., "The molecular pathobiology of cell membrane iron: the sickle red cell as a model" *Free Radic Biol Med* 24: 1040-8 (1998).
Browne et al., "Removal of erythrocyte membrane iron in vivo ameliorates the pathobiology of murine thalassemia," *J Clin Invest* 100: 1459-64 (1997).
Bryant et al., "Pathogen Inactivation The Definitive Safeguard for the Blood Supply," *Arch Pathol Lab Med* 131:719-733 (2007).
Burns et al., "Anaerobic Storage Improves the Mechanical Properties of Stored Red Blood Cells," *Transfusion* 52: 83A (2012).
Burns et al., "Artificial microvascular network: a new tool for measuring rheologic properties of stored red blood cells," *Transfusion*, 52(5):1010-1023 (2012).
Burns et al., "Deterioration of red blood cell mechanical properties is reduced in anaerobic storage," *Blood Transfus* 14: 80-8 (2016).
Buskirk et al., "Accumulation of Biologic Response Modifiers During Red Blood Cell Cold Storage," *Transfusion*, 49(Suppl3): 102A-103A (2009).
Cabrales et al., "Microvascular pressure and functional capillary density in extreme hemodilution with low-and high-viscosity dextran and a low-viscosity Hb-based 02 carrier," *American Journal of Physiology—Heart and Circulatory Physiology* 287: H363-H73 (2004).
Cabrales et al., "Plasma viscosity regulates systemic and microvascular perfusion during acute extreme anemic conditions," *Am J. Physiol Heart Circ Physiol* 291: H2445-52 (2006).
Cannon et al., "Damage control resuscitation in patients with severe traumatic hemorrhage: A practice management guideline from the Eastern.Association for the Surgery of Trauma," *J Trauma Acute Care Surg* 82: 605-17 (2017).
Cap et al., "Whole Blood Transfusion," *Military Medicine* 183, 9/10:44 (2018).
Cardo et al., "Pathogen inactivation of *Leishmania donovani infantum* in plasma and platelet concentrates using riboflavin and ultraviolet light," *Vox Sanguinis* 90:85-91 (2006).
Cardo et al., "Pathogent inactivation of *Trypanosoma cruzi* in plasma and platet concentrates using riboflavin and ultraviolet light," *Transfusion and Apheresis Science* 37:131-137 (2007).
Carmen, "The Selection of Plastic Materials for Blood Bags," *Transfusion Medicine Reviews*, 7(1):1-10 (1993).
Carr et al., "Nonlinear Dynamics of Microvascular Blood Flow," *Annals of Biomedical Engineering*, 28:641-652 (2000).
Cell Deformability, RheoScan (RheoScan-AnD300/RheoScan-D300), obtained on Dec. 11, 2012, from: http://www.rheoscan.com/products/products/products-01.html.
Chanutin et al., "Effect of organic and inorganic phosphates on the oxygen equilibrium of human erythrocytes," *Arch Biochem Biophys* 121: 96-102 (1967).
Chaplin et al., "The Proper Use of Previously Frozen Blood Cells for Transfusion," *Blood*, 59:1118-1120 (1982).

Chatpun et al., "Cardiac mechanoenergetic cost of elevated plasma viscosity after moderate hemodilution," *Biorheology* 47: 225-37 (2010).
Chatpun et al., "Cardiac systolic function recovery after hemorrhage determines survivability during shock," *J Trauma* 70: 787-93 (2011).
Chatpun et al., "Effects of plasma viscosity modulation on cardiac function during moderate hemodilution," *Asian J Transfus Sci* 4: 102-8 (2010).
Chilton et al., "Privacy Protection of Health Information: Patient Rights and Pediatrician Responsibilities," *Pediatrics*, 104(4):973-977 (1999).
Choi et al., "Influence of storage temperature on the responsiveness of human platelets to agonists," *Ann Clin Lab Sci* 33: 79-85 (2003).
Chouchani et al., "Ischaemic accumulation of succinate controls reperfusion injury through mitochondrial ROS," *Nature* 515: 431-5 (2014).
Coene, "Paired analysis of plasma proteins and coagulant capacity after treatment with three methods of pathogen reduction," *Transfusion* 54: 1321-31 (2014).
Cognasse et al., "The role of microparticles in inflammation and transfusion: A concise review," *Transfus. Apher. Sci.* 53(2):159-167 (2015).
Cokelet et al., "Fabrication of in Vitro Microvascular Blood Flow Systems by Photolithography," *Microvascular Research*, 46:394-400 (1993).
Corbin, "Pathogen Inactivation of Blood Components: Current Status and Introduction of an Approach Using Riboflavin as a Photosensitizer," *International Journal of Hematology* Supplement II 76:253-257 (2002).
Cotton et al., "A Randomized Controlled Pilot Trial of Modified Whole Blood Versus Component Therapy in Severely Injured Patients Requiring Large Volume Transfusions," *Annals of Surgery* 258(4) (2013).
Dale et al., "Human Vaccination with *Escherichia coli* J5 Mutant Induces Cross-Reactive Bactericidal Antibody against *Neisseria gonorrhoeae* Lipooligosaccharide," *The Journal of Infectious Diseases*, 166:316-325 (1992).
D'Alessandro et al., "Heterogeneity of blood processing and storage additives in different centers impacts stored red blood cell metabolism as much as storage time: lessons from REDS-1lI-Omics," *Transfusion* 59: 89-100 (2019).
D'Alessandro et al., "Time-course investigation of SAGM-stored leukocyte-filtered red bood cell concentrates: from metabolism to proteomics," *Haematologica* 97: 107-15 (2012).
D'Alessandro et al., "Red blood cell metabolism under prolonged anaerobic storage," *Mol Biosyst* 9: 1196-209 (2013).
D'Alessandro et al., "Red blood cell metabolic responses to refrigerated storage, rejuvenation, and frozen storage," *Transfusion* 57: 1019-30 (2017).
D'Alessandro et al., "Metabolomics of AS-5 RBC supernatants following routine storage," *Vox Sang* (2014).
D'Alessandro et al., "An update on red blood cell storage lesions, as gleaned through biochemistry and omics technologies," *Transfusion* 55: 205-19 (2015).
D'Alessandro et al., "Red blood cell storage and clinical outcomes: new insights," *Blood Transfus* 15: 101-3 (2017).
D'Alessandro et al., "Plasma succinate is a predictor of mortality in critically injured patients," *Journal of Trauma and Acute Care Surgery* 83: 491-5 (2017).
D'Alessandro et al., "Plasma First Resuscitation Reduces Lactate Acidosis, Enhances Redox Homeostasis, Amino Acid and Purine Catabolismin a Rat Model of Profound Hemorrhagic Shock," *Shock* 46: 173-82 (2016).
D'Alessandro et al., "Anaerobic storage Condition enhances GSH Levels while Maintaining Pentose Phosphate Pathway Activity," *Transfusion* 56: 51A (2016).
D'Alessandro et al., "Red blood cell storage in additive solution-7 preserves energy and redox metabolism: a metabolomics approach," *Transfusion* 55: 2955-66 (2015).
D'Alessandro et al., "Routine storage of red blood cell (RBC) units in additive solution-3: a comprehensive investigation of the RBC metabolome," *Transfusion* 55: 1155-68 (2015).

(56) References Cited

OTHER PUBLICATIONS

D'Alessandro et al., "Omics markers of the red cell storage lesion and metabolic linkage," *Blood Transfus* 15: 137-44 (2017).
D'Alessandro et al., "AltitudeOmics: Red Blood Cell Metabolic Adaptation to High Altitude Hypoxia," *J Proteome Res* 15: 3883-95 (2016).
D'Alessandro et al., "Citrate metabolism in red blood cells stored in additive solution-3," *Transfusion* 57: 325-36 (2017).
D'Alessandro et al., "Metabolic effect of alkaline additives and guanosine/gluconate in storage solutions for red blood cells," *Transfusion* 58: 1992-2002 (2018).
D'Alessandro et al., "Effects of aged stored autologous red blood cells on human plasma metabolome," *Blood Adv* 3: 884-96 (2019).
D'Alessandro et al., "Hitchhiker's guide to the red cell storage galaxy: Omics technologies and the quality issue," *Transfus Apher Sci* 56: 248-53 (2017).
D'Amici, et al., "Red blood cell storage in SAGM and AS3: a comparison through the membrane two-dimensional electrophoresis proteome," *Blood Transfusion=Trasfusione del sangue* 10 Suppl 2: s46-54 (2012).
De Angelis et al., "Erythrocyte Shape Control in Stored Blood: The Effect of Additive Solutions on Shape Recovery," *Haematologica*, 73:7-12 (1988).
Deible et al., "Molecular barriers to biomaterial thrombosis by modification of surface proteins with polyethylene glycol," *Biomaterials*, 19:1885-1893 (1998).
de Korte et al., "Prolonged maintenance of 2,3-diphosphoglycerate acid and adenosine triphosphate in red blood cells during storage," *Transfusion*, 48:1081-1089 (2008).
De Venuto et al., "Rejuvenation of Human Red Blood Cells During Liquid Storage," *Transfusion*, 14(4):338-344 (1974).
Delgado et al., "Platelet Function in Stored Whole Blood Measured by a Shear- and Von Willebrand Factor-Dependent Methodology is Retained During Storage at 4° C. for up to 7 Days," *Transfusion* 51: 65A (2011).
Dennis et al., "Transfusion of 2,3 DPG-enriched red blood cells to improve cardiac function," *Ann Thorac Surg* 26: 17-6 (1978).
Dennis et al., "Improved myocardial performance following high 2-3 diphosphoglycerate red cell transfusions," *Surgery* 77: 741-7 (1975).
De Wolski et al., "Metabolic pathways that correlate with post-Transfusion circulation of stored murine red blood cells," *Haematologica* 101: 578-86 (2016).
Dumaswala et al., "Studies in Red Blood Cell Preservation: 9. The Role of Glutamine in Red Cell Preservation," *Vox Sang*, 67:255-259 (1994).
Dumaswala et al., "Glutamine- and Phosphate-Containing Hypotonic Storage Media Better Maintain Erythrocyte Membrane Physical Properties," *Blood*, 88(2):697-704 (1996).
Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).
Dumont et al., "Anaerobic storage of red blood cells in a novel additive solution improves in vivo recovery," *Transfusion*, 49(3):458-464 (2009).
Dumont et al., "Performance Of Anaerobic Stored Red Blood Cells Prepared Using A Prototype 02 & CO2 Depletion And Storage System," *Transfusion* 51s: SP89 (2011).
Dumont et al., "Randomized cross-over in vitro and in vivo evaluation of a prototype anaerobic conditioning and storage system vs. standard aerobic storage," *Vox Sang* 103: 123 (2012).
Dumont et al., "$CO_2$-dependent metabolic modulation in red cells stored under anaerobic conditions," *Transfusion* 56(2): 392-403 (2016)(epub 2015).
Durapore® Membrane Filters—Filter Discs and Membranes, retrieved on Aug. 26, 2014, from: www.emdmillipore.com/US/en/product/Durapore.

Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
Erickson et al., "Evaluation of in vitro Quality of Stored RBC after Treatment with S303 Pathogen Inactivation at Varying Hematocrits," *Transfusion DUP—General Collection* 48(2) Supplement (2008).
European Search Report completed on Feb. 11, 2005, in European Patent Application No. 02 78 2307.9.
European Search Report Jun. 18, 2019, in European Patent Application No. 19163305.6.
Extended European Search Report, dated Aug. 29, 2014 for European Patent Application No. 10823965.8.
Extended European Search Report dated Oct. 30, 2014 in European Patent Application No. 11838889.1.
Extended European Search Report dated Oct. 24, 2014 in European Patent Application No. 12807324.4.
Extended European Search Report dated Mar. 5, 2015, in European Patent Application No. 12821624.9.
Extended European Search Report dated Jun. 15, 2015, in European Patent Application No. 11820660.6.
Extended European Search Report dated Oct. 9, 2018, in European Patent Application No. 16784043.8.
Extended European Search Report dated Apr. 16, 2019, in European Patent Application No. 16845192.0.
Extended European Search Report dated Jun. 5, 2019, in European Patent Application No. 19158815.1.
Extended European Search Report dated Feb. 21, 2022 in European Patent Application No. 21199989.1.
Ezuki et al., "Survival and recoery of apheresis platelets stored in a polyolefin container with high oxygen permeability," *Vox Sanguinis* 94:292-298 (2008).
Fahraeus et al., "The Viscosity of the Blood in Narrow Capillary Tubes," *Am. J. Physiol.*, 96(3):562-568 (1931).
Fage et al., "On transition from laminar to turbulent flow in the boundary layer," The gamma-ray transition of radio-bromine, *Proceedings of the Royal Society*, 178(973):205-227 (1940).
Fang et al., "Inhibition of Lipopolysaccharide-Associated Endotoxin Activities In Vitro and In Vivo by the Human Anti-Lipid A Monoclonal Antibody SdJ5-1.17.15," *Infection and Immunity*, 61(9):3873-3878 (1993).
Farber et al., "Effect of decreased 02 affinity of hemoglobin on work performance during exercise in healthy humans," *J Lab Clin Med* 104: 166-75 (1984).
Fast et al., "Inactivation of Human White Blood Cells in Red Blood Cell Products Using the MIRASOL® System for Whole Blood," *Blood* Abstract #2897 110(11)(pt. 1) (2007).
Fatouros et al., "Recombinant factor VII SQ—influence of oxygen, metal ions, pH and ionic strength on its stability in aqueous solution," *International Journal of Pharmaceutics*, 155(1):121-131 (1997).
Feys, "Oxygen removal during pathogen inactivation with riboflavin and UV light preserves protein function in plasma for Transfusion," *Vox Sang* 106: 307-15 (2013).
Frame et al., "A System for Culture of Endothelial Cells in 20-50-μm Branching Tubes," *Microcirculation*, 2(4):377-385 (1995).
"Friction Factor for Flow in Coils and Curved Pipe," Neutrium Available on the world wide web at neutrium.net/fluid_flow/friction-factor-for-flow-in-coils-and-curved-pipe/ (2017).
Friesenecker et al., "Arteriolar vasoconstrictive response: comparing the effects of arginine vasopressin and norepinephrine," *Crit Care* 10: R75 (2006).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).
Gardner, "Problems of Multiple Transfusions," *Official Journal of the California Medical Associate*, 83(2):93-97 (1958).
Gehrke et al., "Metabolomics evaluation of early-storage red blood cell rejuvenation at 4 degrees C and 37 degrees C," *Transfusion* 58: 1980-91 (2018).

(56) References Cited

OTHER PUBLICATIONS

Gevi et al., "Alterations of red blood cell metabolome during cold liquid storage of erythrocyte concentrates in CPD-SAGM," *J Proteomics* 76 Spec No. 168-180 (2012).
Gifford et al, "Parallel Microchannel-Based Measurements of Individual Erythrocyte Areas and Volumes," *Biophysical Journal*, 84:623-633 (2003).
Gifford et al, "A detailed study of time-dependent changes in human red blood cells: from reticulocyte maturation to erythrocyte senescence," *British Journal of Haematology*, 135:395-404 (2006).
Golan et al., "Transfusion of fresh whole blood stored (4 degrees C) for short period fails to improve platelet aggregation on extracellular matrix and clinical hemostasis after cardiopulmonary bypass," *J Thorac Cardiovasc Surg* 99: 354-60 (1990).
Goodrich, "The Use of Riboflavin for the Inactivation of Pathogens in Blood Products," *Vox Sanguinis* Suppl. 2 78:211-215 (2000).
Green et al., "10. Liposomal Vaccines," Immunobiology of Proteins and Peptides VII, Plenum Press, New York, pp. 83-92 (1995).
Greenwalt et al., "Studies In Red Blood Cell Preservation. 7. In vivo and in Vitro Studies with a Modified Phosphate-Ammonium Additive Solution," *Vox Sang*, 65:87-94 (1993).
Greenwalt et al., "Studies in Red Blood Cell Preservation. 8. Liquid Storage of Red Cells in Glycerol-Containing Additive Solution," *Vox. Sang*, 67:139-143 (1994).
Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).
Greenwalt et al., "The effect of hypotonicity, glutamine, and glycine on red cell preservation," *Transfusion*, 37:269-276 (1997).
Griffith, "Temporal chaos in the microcirculation," *Cardiovascular Research*, 31:342-358 (1996).
Grigioni et al., "A discussion on the threshold limited for nemo lysis related to Reynolds shear stress," *J. Biomech.*, 32:1107-1112 (1999).
Gulliksson et al., "Storage of whole blood overnight in different blood bags preceding preparation of blood components: in vitro effects on red blood cells," *Blood Transfus* 7:210-215 (2009).
Haddaway et al., "Hemostatic properties of cold-stored whole blood leukoreduced using a platelet-sparing versus a non-platelet-sparing filter," *Transfusion* (2019).
Hamasaki et al., "Acid-citrate-dextrose-phosphoenolpyruvate medium as a rejuvenant for blood storage," *Transfusion*, 23(1):1-7 (1983).
Heaton et al., "Use of Adsol preservation solution for prolonged storage of low viscosity AS-1 red blood cells," *Br J. Haematol*, 57(3):467-478 (1984).
Hebbel, et al., Oxidation-induced changes in microrheologic properties of the red blood cell membrane. *Blood* 1990;76: 1015-20.
Hebbel, "Auto-oxidation and a membrane-associated 'Fenton reagent': a possible explanation for development of membrane lesions in sickle erythrocytes," *Clin Haematol* 14: 129-40 (1985).
Henschler et al., "Development of the S-303 Pathogen Inactivation Technology for Red Blood Cell Concentrates," *Transfusion Medicine and Hemotherapy* 38(1):33-42 (2011).
Hershko, "Mechanism of iron toxicity and its possible role in red cell membrane damage," *Semin Hematol* 26: 277-85 (1989).
Hess, "Extended Liquid Storage of Red Blood Cells," Blood Donors and the Supply of Blood and Blood Products, National Academy Press, Washington, D.C., pp. 99-102 (1996).
Hess et al., "Successful storage of RBCs for 9 weeks in a new additive solution," *Transfusion*, 40:1007-1011 (2000).
Hess, "Storage of red blood cells under anaerobic conditions," *Vox Sanguinis*, 93:183 (2007).
Hess et al., "Alkaline CPD and the preservation of RBC 2,3-DPG," *Transfusion*, 42:747-752 (2002).
Hess et al., "Storage of Red Blood Cells: New Approaches," *Transfusion Medicine Reviews*, 16(4):283-295 (2002).
Hess et al., "Advances in military, field, and austere Transfusion medicine in the last decade," *Transfus Apher Sci* 49: 380-6 (2013).
Hodgson et al., "Prophylactic use of human endotoxin-core hyperimmune gammaglobulin to prevent endotoxaemia in colostrum-deprived, gnotobiotic lambs challenged orally with *Escherichia coli*," *FEMS Immunology and Medical Microbiology*, 11:171-180 (1995).
Högman et al., "Cell Shape and Total Adenylate Concentration as Important Factors for Posttransfusion Survival of Erythrocytes," *Biomed. Biochim. Acta*, 42:S327-S331 (1983).
Högman et al., "Effects of Oxygen on Red Cells during Liquid Storage at +4° C.," *Vox Sang.*, 51:27-34 (1986).
Högman et al., "Effects of oxygen and mixing on red cells stored in plastic bags at +4° C.," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).
Högman, "Preparation and Preservation of Red Cells," *Vox Sanguinis* 74(Suppl. 2):177-187 (1998).
Holme et al., "Current Issues Related to the Quality of Stored RBCs," *Transfusion and Apheresis Science*, 33(1):55-61 (2005).
Hornsey et al., "Cold storage of pooled, buffy-coat-derived, leucoreduced platelets in plasma," *Vox Sang* 95 26-32 (2008).
Huang et al., "Continuous Particle Separation Through Deterministic Lateral Displacement," *Science*, 304:987-990 (2004).
International Committee for Standardization in Hematology, "Recommended Methods for Radioisotope Red Cell Survival Studies," *Blood* 38(3):378-386 (1971).
International Preliminary Report on Patentability dated Feb. 18, 2011 (completed on Feb. 8, 2012), in International Patent Application No. PCT/US2010/52084.
International Preliminary Report on Patentability dated May 24, 2012 (completed on May 21, 2012), in International Patent Application No. PCT/US2010/52376.
International Search report Completed on Feb. 8, 2011, in International Patent Application No. PCT/US10/52084.
International Preliminary Report on Patentability completed on Oct. 18, 2011, in International Patent Application No. PCT/US2010/031055.
International Search Report completed on Jul. 8, 1996, in International Patent Application No. PCT/US96/09005.
International Search Report completed on Nov. 10, 2003, in International Patent Application No. PCT/US02/36735.
International Search Report completed on May 20, 2010, in International Patent Application No. PCT/US2010/31055.
International Search Report and Written Opinion dated Dec. 6, 2010 for corresponding International Patent Application No. PCT/US2010/052376.
International Search Report dated Apr. 27, 2011(completed on Apr. 26, 2011), in International Patent Application No. PCT/US2010/044045.
International Search Report completed on Dec. 21, 2011, in International Patent Application No. PCT/US11/49168.
International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
International Search Report and Written Opinion issued in International Application PCT/US2014/019537 dated Jul. 10, 2014.
International Search Report completed on Nov. 9, 2012 issued in International Patent Application No. PCT/US12/045426 (mailed Nov. 26, 2012).
International Search Report for PCT/US2016/021794 dated Jul. 18, 2016.
International Search Report for PCT/US2016/033151 dated Oct. 13, 2016.
International Search Report for PCT/US2016/051115 dated Nov. 21, 2016.
International Search Report for PCT/US2017/034410 dated Dec. 22, 2017.
International Search Report for PCT/US2020/057754 dated Feb. 15, 2021.

(56) References Cited

OTHER PUBLICATIONS

Irsch et al., "Pathogen inactivation of platelet and plasma blood components for transfusion using the INTERCEPT Blood System™," *Transfusion Medicine and Hemotherapy*, 38:19-31 (2011).
Jagannathan et al., "Oxidative stress under ambient and physiological oxygen tension in tissue culture," *Curr Pharmacol Rep* 2: 64-72 (2016).
Jain et al., "Determinants of Leukocyte Margination in Rectangular Microchannels," *PLoS ONE*, 4(9):1-8 (2009).
Janetzko et al., "Pathogen reduction technology (Mirasol®) treated singledonor platelets resuspended in a mixture of autologous plasma and PAS," *Vox Sanguinis* 97:234-239 (2009).
Jarman et al., "Rural risk: Geographic disparities in trauma mortality," *Surgery* 160: 1551-9 (2016).
Jarolim et al., "Effect of hemoglobin oxidation products on the stability of red cell membrane skeletons and the associations of skeletal proteins: correlation with a release of them in," *Blood* 76: 2125-31 (1990).
Jarus et al., "Barrier Properties of polypropylene/polyamide blends produced by microlayer coextrusion," *Polymer* 43:2401-2408 (2002).
Jayasinghe et al., "Controlled deposition of nanoparticle clusters by electrohydrodynamic atomization," *Nanotechnology*, 15:1519-1523 (2004).
Jenkins et al., "Trauma hemostasis and oxygenation research position paper on remote damage control resuscitation: definitions, current practice, and knowledge gaps," *Shock* 41 Suppl 1: 3-12 (2014).
Jesch et al., "Oxygen dissociation after Transfusion of blood stored in ACD or CPD solution," *J Thorac Cardiovasc Surg* 70: 35-9 (1975).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Jobes et al., "Toward a definition of "fresh" whole blood: an in vitro characterization of coagulation properties in refrigerated whole blood for Transfusion," *Transfusion* 51: 43-51 (2011).
Johnson et al., "Regulation of blood flow in single capillaries," *American Journal of Physiology*, 212:1405-1415 (1967).
Jy et al., "Release of Microparticles During Blood Storage Is Influenced by Residual Platelets, Leukocytes and Oxygen Levels," *Blood* 120: 3435 (2012).
Kaihara et al., "Silicon Micromachining to Tissue Engineer Branched Vascular Channels for Liver Fabrication," *Tissue Engineering*, 6(2):105-117 (2000).
Kaiser-Guignard et al., "The clinical and biological impact of new pathogen inactivation technologies on platelet concentrates," *Blood Reviews* 28:235-241 (2014).
Kakaiya et al., "Platelet preservation in large containers," *Vox Sanguinis*, 46(2):111-118 (1984).
Kerger et al., "Systemic and subcutaneous microvascular pO2 dissociation during 4-h hemorrhagic shock in conscious hamsters," *Am J. Physiol* 270: H827-H36 (1996).
Khorana et al., "Blood Transfusions, thrombosis, and mortality in hospitalized patients with cancer," *Arch Intern Med* 168: 2377-81 (2008).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Kilkson et al., "Platelet metabolism during storage of platelet concentrates at 22° C.," *Blood* 64(2):406-414 (1984).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).

Kohli et al., "Packed red cells versus whole blood transfusion for severe paediatric anaemia, pregnancy-related anaemia and obstetric bleeding: an analysis of clinical proactice buidelines from sub-Saharan Africa and evidence underpinning recommendments," *Tropical Medicine and International Health* 24(1):11-22 (2019).
Korsten et al., "Determination of %5O2 in More Than 1300 Fresh Erythrocyte Concentrates by Resonance Raman Spectroscopy," *Transfusion* 58: 215A (2018).
Kotwal et al., "The Effect of a Golden Hour Policy on the Morbidity and Mortality of Combat Casualties," *JAMA Surg* 151: 15-24 (2016).
Kreuger et al., "A clinical evaluation of citrate-phosphate-dextrose-adenine blood," *Vox Sang* 29: 81-9 (1975).
Krogh, "Studies on the physiology of capillaries. II. The reactions to local stimuli of the blood-vessels in the skin and web of the frog," *The Journal of Physiology*, 55:412-422 (1921).
Kuraoka, et al., "Ship-in-a-bottle synthesis of a cobalt phthalocyanine/porous glass composite membrane for oxygen separation," *Journal of Membrane Science*, 286(1-2):12-14 (2006).
Kwan et al., "Microfluidic analysis of cellular deformability of normal and oxidatively damaged redd blood cells," *Am J Hematol* 88: 682-9 (2013).
Kynar Flex Product Catalog, downloaded May 20, 2015 from Kynar.com.
Liu et al., "Beneficial Role of Erythrocyte Adenosine A2B Receptor-Mediated AMP-Activated Protein Kinase Activation in High-Altitude Hypoxia," *Circulation* 134: 405-21 (2016).
Lowndes, "Blood Interference in fluorescence spectrum: Experiment, analysis and comparison with intraoperative measurements on brain tumor," *Bachelor Thesis*, Linköping University, pp. 1-42 (2010).
Lozono et al., "Pathogen inactivation: coming of age," *Curr Opin Hematol* 20(6):540-545 (2013).
Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).
Lundblad, "Factor VIII—Reducing agents, copper ions, and stability," http://lundbladbiotech.com.
Manno et al., "Comparison of the hemostatic effects of fresh whole blood, stored whole blood, and components after open heart surgery in children," *Blood* 77: 930-6 (1991).
Mazor et al., "Prolonged Storage of Red Cells: The Effect of pH, Adenine Phosphate," *Vox Sanguinis*, 66:264-269 (1994).
McDonald et al., "Poly(dimethylsiloxane) as a Material for Fabricating Microfluidic Devices," *Accounts of Chemical Research*, 35(7):491-499 (2002).
Meryman et al., "Prolonged storage of red cells at 4° C.," *Transfusion*, 26(6):500-505 (1986).
Meryman et al., "Extending the storage of red cells at 4° C.," *Transfus. Sci.*, 15(2):105-115 (1994).
Miller, "New evidence in trauma resuscitation—is 1: 1: 1 the answer?" *Perioperative medicine* 2: 13 (2013).
Moll et al., "Dean vortices applied to membrane process. Part II: Numerical approach," *Journal of Membrane Science*, 288:321-335 (2007).
Mollison, "The Introduction of Citrate as an Anticoagulant for Transfusion and of Glucose as a Red Cell Preservative," *British Journal of Haematology* 108:1318 (2000).
Moroff et al., "Factors Influencing Changes in pH during Storage of Platelet Concentrates at 20-24° C.," *Vox Sanguinis*, 42(1):33-45 (1982).
Moroff et al., "Proposed standardization of methods for determining the 24-hour survival of stored red cells," *Transfusion*, 24:109-114 (1984).
Moroff et al., "Concepts about current conditions for the preparation and storage of platelets," *Transfus Med Rev* V(1):48-59 (1991).
Mufti, "Treatment of whole blood (WB) and red blood cells (RBC) with S-303 inactivates pathogens and retains in vitro quality of stored RBC," *Biologicals* 38:14-19 (2010).

(56) References Cited

OTHER PUBLICATIONS

Murphy et al., "Platelet storage at 22° C.: role of gas transport across plastic containers in maintenance of viability," *Blood* 46(2):209-218 (1975).
Murphy et al., "Increased Mortality, Postoperative Morbidity, and Cost After Red Blood Cell Transfusion in Patients Having Cardiac Surgery," *Circulation*, 116:2544-2552 (2007).
Musante et al., "Active Focal Segmental Glomerulosclerosis is Associated with Massive Oxidation of Plasma Albumin," *Journal of the American Society of Nephrology*, 18(3):799-810 (2007).
Mussano et al., "Cytokine, chemokine and growth factor profile of Platelet Rich Plasma," *Universita Degli Studi Di Tornio* 2016.
Nair et al., "Cold-Stored Platelets in PAS Exhibit Superior Hemostatic Potential" *Blood* 126: 772 (2015) Abstract.
Nemkov et al., "Metabolomics in Transfusion medicine," *Transfusion* 56: 980-93 (2015).
Nemkov et al., "Hypoxia modulates the purine salvage pathway and decreases red blood cell and supernatant levels of hypoxanthine during refrigerated storage," *Haematologica* 103: 361-72 (2018).
Nemkov et al., "Metabolism of Citrate and Other Carboxylic Acids in Erythrocytes As a Function of Oxygen Saturation and Refrigerated Storage," *Front Med (Lausanne)* 4: 175 (2017).
Nessen et al., "Fresh whole blood use by forward surgical teams in Afghanistan is associated with improved survival compared to component therapy without platelets," *Transfusion* 53:107S-113S (2013).
Ng et al., "Components for integrated poly(dimethylsiloxane) microfluidic systems," *Electrophoresis*, 23:3461-3473 (2002).
Nilsson et al., "Association between venous thromboembolism and perioperative allogeneic Transfusion," *Arch Surg* 142: 126-32; discussion 33 (2007).
Ohkuma et al., "The preservative-exchange method using a sextuple-bag system for a 10-week storage period of red blood cells," *Transfusion Medicine*, 1:257-262 (1991).
Paglia et al., "Biomarkers defining the metabolic age of red blood cells during cold storage," *Blood* 128: e43-50 (2016).
Paillous et al. "Mechanisms of photosensitized DNA cleavage," *J. Photochem. Photobiol. B: Biol.* 20:203-209 (1993).
Pallotta et al., "Storing red blood cells with vitamin C and N-acetylcysteine prevents oxidative stress-related lesions: a metabolomics overview," *Blood Transfus* 12: 376-87 (2014).
Pallotta et al., "Supplementation of anti-oxidants in leucofiltered erythrocyte concentrates: assessment of morphological changes through scanning electron microscopy," *Blood Transfus* 12: 421-4 (2014).
Parkkinen et al., "Plasma ascorbate protects coagulation factors against photooxidation," *Thromb Haemost* 75(2):292-297 (1996).
Peirce et al., "The Membrane Lung: Studies with a New High Permeability Co-Polymer Membrane," *Trans. Amer. Soc. Artif. Int. Organs* vol. XIV:220-226 (1968).
Pelletier et al., "Pathogen inactivation techniques," *Best Practice & Research Clinical Haematology* 19(1):205-242 (2006).
Picker et al., "Current methods for the reduction of blood-borne pathogens: a comprehensive literature review," *Blood Transfusion* 11:343-348 (2013).
Pidcoke et al., "Tenyear analysis of Transfusion in Operation Iraqi Freedom and Operation Enduring Freedom: increased plasma and platelet use correlates with improved survival," *Journal of Trauma and Acute Care Surgery*;73: S445-S52 (2012).
Pidcoke et al., "Primary hemostatic capacity of whole blood: a comprehensive analysis of pathogen reduction and refrigeration effects over time," *Transfusion* 53:137S-149S (2013).
Poncelet et al., "Tips and tricks for flow cytometry-based analysis and counting of microparticles," *Transfus. Apher. Sci.* 53(2):110-126 (2015).
Poxton, "Antibodies to lipopolysaccharide," *Journal of Immunological Methods*, 186:1-15 (1995).
Prefiltration before membrane filtration, hydrophobic, 25 µm 142 mm, retrieved on Aug. 26, 2014, from: www.emdmillipore.com/US/en/product/Prefiltration-before-membrane-filtration.

Pries et al., "Biophysical aspects of blood flow in the microvasculature," *Cardiovascular Research*, 32:654-667 (1996).
Prowse et al., "Commercially available blood storage containers," *Vox Sanguinis* 106(1): 1-13 (2014).
Prudent, et al., "Oxygen in Red Blood Cell Concentrates Influence of Donor's Characteristics, Location and Blood Processing," *Vox Sang* 113: 116 (2018).
Przepiorka et al. "Use of Irradiated Blood components: Practice Parameter," *Am J Clin Pathol* 106(1):6-11 (1996).
Ramstack et al., "Shear-induced activation of platelets," *J. Biomech.*, 12:113-125 (1979).
Reisz et al., "Red blood cells in hemorrhagic shock: a critical role for glutaminolysis in fueling alanine transamination in rats," *Blood Advances* 1:1296-305 (2017).
Reisz et al., "Methylation of protein aspartates and deamidated asparagines as a function of blood bank storage and oxidative stress in human red blood cells," *Transfusion* 58: 2978-91 (2018).
Reisz et al., "Metabolic Linkage and Correlations to Storage Capacity in Erythrocytes from Glucose 6-Phosphate Dehydrogenase-Deficient Donors," *Front Med (Lausanne)* 4: 248 (2017).
Reisz et al., "Oxidative modifications of glyceraldehyde 3-phosphate dehydrogenase regulate metabolic reprogramming of stored red blood cells," *Blood* 128: e32-42 (2016).
Reynolds et al., "S-nitrosohemoglobin deficiency: A mechanism for loss of physiological activity in banked blood," *Proceedings of the National Academy of Sciences*, 104(43):17058-17062 (2007).
Risbano et al., "Effects of Aged Stored Autologous Red Blood Cells on Human Endothelial Function," *Am J Respir Crit Care Med* 192: 1223-33 (2015).
Rock et al., "Nutricel as an additive solution for neonatal transfusion," *Transfusion Science*, 20:29-36 (1999).
Rolfsson et al., "Metabolomics comparison of red cells stored in four additive solutions reveals differences in citrate anticoagulant permeability and metabolism," *Vox Sang* (2017).
Sambuceti et al., "Why should we study the coronary microcirculation?," *Am J Physiol Heart Circ Physiol*, 279:H2581-H2584 (2000).
Schubert et al., "Whole blood treated with riboflavin and ultraviolet light: Quality assessment of all blood components produced by the buffy coat method," *Transfusion* 55(4):815-823 (2014).
Scott et al., "Effect of excess alpha-hemoglobin chains on cellular and membrane oxidation in model beta-thalassemic erythrocytes," *J Clin Invest* 91: 1706-12 (1993).
Seghatchian et al., "Pathogen-reduction systems for blood components: The current position and future trends," *Transfusion and Apheresis Science* 35:189-196 (2006).
Seghatchian, "Pathogen inactivation of whole blood and red cell components: An overview of concept, design, developments, criteria of acceptability and storage lesion," *Transfusion and Apheresis Science* 49:357-363 (2013).
Seok et al., "Genomic responses in mouse models poorly mimic human inflammatory diseases," *Proceedings of the National Academy of Sciences* 110: 3507-12 (2013).
Sivertsen et al., "Preparation of leukoreduced whole blood for Transfusion in austere environments; effects of forced filtration, storage agitation, and high temperatures on hemostatic function," *J Trauma Acute Care Surg* 84: S93-S103 (2018).
Shalev et al., "Extremely high avidity association of Fe(III) with the sickle red cell membrane," *Blood* 88: 349-52 (1996).
Shapiro, "To filter blood or universal leukoreduction: what is the answer?," *Critical Care* 8(Suppl 2): S27-draftS30 (2004).
Sheffield et al., "Changes in coagulation factor activity and content of di(2-ethylhexyl) phthate in frozen plasma units during refrigerated storage for up to 5 days after thawing," *Transfusion*, 52:494-502 (2012).
Shevkoplyas et al., "Direct measurement of the impact of impaired erythrocyte deformability on microvascular network perfusion in a microfluidic device," *Lab Chip*, 6:914-920 (2006).
Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).

(56) References Cited

OTHER PUBLICATIONS

Snyder et al., "In vitro and in vivo evaluation of a whole blood platelet-sparing leukoreduction filtration system," *Transfusion* 50:2145-51 (2010).
Sohmer et al., "Phosphoenolypyruvate (PEP) Effects on Fresh and Stored Red Blood Cells," *Proceedings of the Society for Experimental Biology and Medicine*, 171:24-33 (1982).
Spinella et al., "Prehospital hemostatic resuscitation to achieve zero preventable deaths after traumatic injury," *Curr Opin Hematol* (2017).
Spinella et al., "Whole blood: back to the future," *Curr Opin Hematol* 23: 536-42 (2016).
Spinella et al., "Whole blood for hemostatic resuscitation of major bleeding," *Transfusion* 56:S190-S202 (2016).
Steurer et al., "Trauma and Massive Blood Transfusions," *Curr. Anesthesiol. Rep* 4:200-208 (2014).
Strandenes et al., "Emergency Whole-Blood Use in the Field: a Simplified Protocol for Collection and Transfusion," *SHOCK* 41(Suppl 1):76-83 (2014).
Strandenes et al., "Low Titer Group O Whole Blood in Emergency Situations," *SCHOCK* 41(Suppl 1): 70-75 (2014).
Su et al., "Impermeable barrier films and protective coatings based on reduced graphene oxide," *Nature Communications* 5 Article No. 4843 (2014).
Sun et al., "Purinergic control of red blood cell metabolism: novel strategies to improve red cell storage quality," *Blood Transfus* 15: 535-42 (2017).
Sun, et al., "Sphingosine-1-phosphate promotes erythrocyte glycolysis and oxygen release for adaptation to high-altitude hypoxia," *Nat Commun* 7: 12086 (2016).
Supplementary European Search Report dated Jan. 20, 2015 in European Patent Application No. 12822378.2.
Sutera et al., "Deformation and Fragmentation of Human Red Blood Cells in Turbulent Shear Flow," *Biophys. J.*, 15:1-10 (1975).
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-day-old AS-1 RBCs," *Transfusion*, 41:550-555 (2001).
Tannahill et al., "Succinate is an inflammatory signal that induces IL-1beta through HIF-1alpha" *Nature* 496: 238-42 (2013).
Teisseire et al., "Induced low P50 in anesthetized rats: blood gas, circulatory and metabolic adjustments," *Respir Physiol* 58: 335-44 (1984).
Tinmouth et al., "The Clinical Consequences of the Red Cell Storage Lesion," *Transfusion Medicine Reviews*, 15(2):91-107 (2001).
Tolinski, "Getting the Most out of Polypropylene, Polyethylene and TPO," *Additives for Polyolefins*, Second Edition 2015.
Tracey et al., "A Silicon Micromachined Device for Use in Blood Cell Deformability Studies," *IEEE Transactions on Biomedical Engineering*, 42(8):751-761 (1995).
"Transition and Turbulence," https://www.princeton.edu/~asmits/Bicycle_web/transition.html . Adapted from The Engine and the Atmosphere: An Introduction to Engineering by Z. Warhaft, Cambridge University Press, (1997).
Tsai et al., "Microvascular perfusion upon exchange Transfusion with stored red blood cells in normovolemic anemic conditions," *Transfusion* 44: 1626-34 (2004).
Tsantes et al., "Redox imbalance, macrocytosis, and RBC homeostasis," *Antioxid Redox Signal* 8: 1205-16 (2006).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "Improved oxygen delivery to the myocardium during hypothermia by perfusion with 2,3 DPG-enriched red blood cells," *Am Thorac Surg* 30: 527-35 (1980).
Valeri, "Circulation and hemostatic effectiveness of platelets stored at 4 C or 22 C: studies in aspirintreated normal volunteers," *Transfusion* 16: 20-3 (1976).

Valeri, "Hemostatic effectiveness of liquid-preserved and previously frozen human platelets," *N Engl J Med* 290: 353-8 (1974).
Valeri et al., "The survival, function, and hemolysis of human RBCs stored at 4° C. in additive solution (AS-1, AS-3, or AS-5) for 42 days and then biochemically modified, frozen, thawed, washed, and stored at 4° C. in sodium chloride and glucose solution for 24 hours," *Transfusion*, 40:1341-1345 (2000).
Van Buskirk et al., "Comparison of Cytokine, Cell-free Hemoglobin, and Isoprostane Accumulations in Packed Red Blood Cells During Novel Anaerobic and Conventional Cold Storage," *Transfusion* 54S: SP53 (2014).
Van Buskirk et al., "Comparison of microparticles production in packed red blood cells stored under anaerobic and conventional cold storage condition," *Vox Sang* 105 (S1): 150 (2007).
Van Buskirk et al., "Evaluation of Select Red Blood Cell Biochemical and Coagulation Properties in Whole Blood Stored Using a Novel Anaerobic Storage Platform," *Transfusion* 56: 54A (2016).
Van der Meer et al., "Platelet preservation: Agitation and containers," *Transfusion and Apheresis Science* 44:297-304 (2011).
Van Slyke, "An Apparatus for Determination of the Gases in Blood and Other Solutions," *Chemistry* 7:229-231 (1921).
Voigt et al., "Effects of a restrictive Blood Transfusion protocol on acute pediatric burn care: Transfusion threshold in pediatric burns," *J Trauma Acute Care Surg* 85: 1048-54 (2018).
Vrielink et al., "Transfusion-transmissible infections," *Current Opinion in Hematology* 5:396-405 (1998).
Wallvik et al., "Platelet Concentrates Stored at 22° C. Need Oxygen the Significance of Plastics in Platelet Preservation," *Vox Sanguinis*, 45(4):303-311 (1983).
Wallvik et al., "The platelet storage capability of different plastic containers," *Vox Sanguinis*, 58(1):40-44 (1990).
Wang et al., "Fabrication of PLGA microvessel scaffolds with circular microchannels using soft lithography," *Journal of Micromechanics and Microengineering*, 17(10):2000-2005 (2007).
Wang et al., "The contribution of oxidative stress to platelet senescence during storage" *Transfusion* (2019).
Weinberg et al., "Transfusions in the Less Severely Injured: Does Age of Transfused Blood Affect Outcomes?," *The Journal of Trauma*, 65(4):794-798 (2008).
Wilding et al., "Manipulation and Flow of Biological Fuids in Straight Channels Micromachined in Silicon," *Clinical Chemistry*, 40(1):43-47 (1994).
Williams, "Blood Transfusion on Cruise Ships; A 36 Month Review of Preliminary Data," *THOR Trauma Hemostasis & Oxygenation Research Network, RDCR Symposium, Bergen* (2013).
Williams et al., "Transfusion of Anaerobically Stored Red Blood Cells Improves Recovery in Experimental Rat Hemorrhagic Shock Model," *Transfusion* 57: 33A (2017).
Williams et al., "Transfusion of Anaerobically Stored Red Blood Cells Improves Recovery in Experimental Rat Hemorrhagic Shock Model," *Shock Abstract* (2019).
Winter, "Red blood cell in vitro quality and function is maintained after S-303 pathogen inactivation treatment," *Transfusion* 54:1798-1807 (2014).
Wolfe et al., "Molecular defect in the membrane skeleton of blood bank-stored red cells. Abnormal spectrin-protein 4.1-actin complex formation," *J Clin Invest* 78: 1681-6 (1986).
Wolfe, "Oxidative injuries to the red cell membrane during conventional blood preservation," *Semin Hematol* 26: 307-12 (1989).
Wood et al., "The Viability of Human Blood Stored in Phosphate Adenine Media," *Transfusion* 7, 401-408 (1967).
Woodson, "Functional consequences of altered blood oxygen affinity," *Acta Biol Med Ger* 40: 733-6 (1981).
Wu et al., "Polymer microchips bonded by $O_2$-plasma activation," *Electrophoresis*, 23:782-790 (2002).
Yalcin et al., "Increased hemoglobin 02 affinity protects during acute hypoxia," *Am J. Physiol Heart Circ Physiol* 303: H271-81 (2012).
Yazer et al., "Coagulation factor levels in plasma frozen within 24 hours of phlebotomy over 5 days of storage at 1 to 6° C.," *Transfusion*, 48:2525-2530 (2008).
Yhap et al., "Decreased oxygen uptake with stored blood in the isolated hindlimb" *J Appl Physiol* 38: 882-885 (1975).

(56) References Cited

OTHER PUBLICATIONS

Yoshida et al., "Extended storage of red blood cells under anaerobic conditions," *Vox Sanguinis*, 92:22-31 (2007).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Yoshida et al., "Anaerobic storage of red blood cells," *Blood Transfus*, 8:220-236 (2010).
Yoshida et al., "Oxygen content—uncontrolled and overlooked parameter associated with stored red cell concentrate: Unexpectedly wide distribution," *Vox Sang* 112: P-244 (2017) Abstract.
Yoshida et al., "Enhancing uniformity and overall quality of red cell concentrate with anaerobic storage," *Blood Transfus* 15: 172-81 (2017).
Yoshida et al., "Toward a comprehensive biochemical model of human erythrocyte: relationship between metabolic and osmotic state of the cell and the state of hemoglobin," *Prog Clin Biol Res* 319: 179-93; discussion 94-6 (1989).
Yoshida et al., "Unexpected Variability of Hemoglobin Oxygen Saturation in Packed Red Blood Cells upon Donation Suggests Uncontrolled and Overlooked Parameter Associated with the Development of the Storage Lesion," *Transfusion* 57 (2017).
Yoshida et al., "Red blood cell storage lesion: causes and potential clinical consequences" *Blood Transfus* 17: 27-52 (2019).
Yoshida et al., "Reduction of Microparticle Generation During Anaerobic Storage of Red Blood Cells," *Transfusion* 52: 83A (2012).
Yuasa et al., "Improved extension of platelet storage in a polyolefin container with higher oxygen permeability," *British Journal of Hematology* 126:153-159 (2004).
Zaroulis, et al., "Lactic acidemia in baboons after Transfusion of red blood cells with improved oxygen transport function and exposure to severe arterial hypoxemia," *Transfusion* 19: 420-5 (1979).
Zavizion et al., "Inactivation of mycoplasma species in blood by INACTINE PEN110 process," *Transfusion* 44:286-293 (2004).
Zhang et al., "Modification of Si(100) surface by the grafting of poly(ethylene glycol) for reduction in protein adsorption and platelet adhesion," *J Biomed Mater Res*, 56:324-332 (2001).
Zielinski et al., "Back to the future: The renaissance of whole-blood transfusions for massively hemorrhaging patients," *Surgery* 155(5) 883-886 (2014).
Zielinski, et al., "Prehospital Blood Transfusion programs: Capabilities and lessons learned," *J Trauma Acute Care Surg* 82: S70-s8 (2017).
Zimrin et al., "Current issues relating to the transfusion of stored red blood cells," *Vox Sanguinis*, 96:93-103 (2009).
Zimring et al., "Established and theoretical factors to consider in assessing the red cell storage lesion," *Blood*, 125:2185-2190 (2015).
Zingarelli et al., "Part I: Minimum Quality Threshold in Preclinical Sepsis Studies (MQTiPSS) for study design and humane modeling endpoints," *Shock* 51: 10-22 (2019).
Zink et al., "Noninvasive Evaluation of Active Lower Gastrointestinal Bleeding: Comparison Between Contrast-Enhanced MDCT and 99mTcLabeled RBC Scintigraphy," *American Journal of Roentgenology* 191: 1107-14 (2008).
Zinkham et al., "Carboxyhemoglobin levels in an unstable hemoglobin disorder (Hb Zurich): effect on phenotypic expression," *Science* 209: 406-8 (1980).
Zolla et al., "Classic and alternative red blood cell storage strategies: seven years of '-omics' investigations," *Blood Transfus* 13:21-31 (2015).

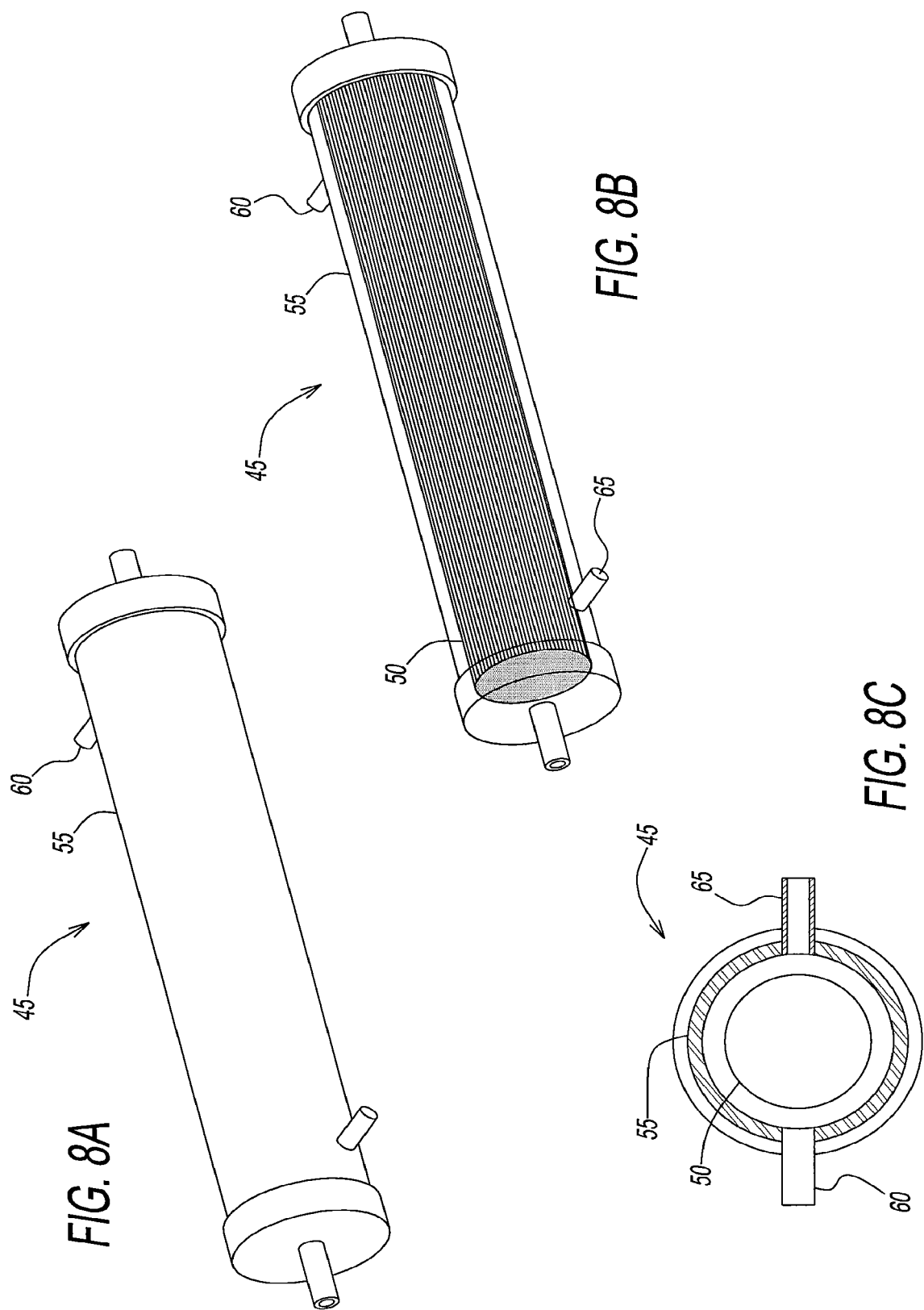

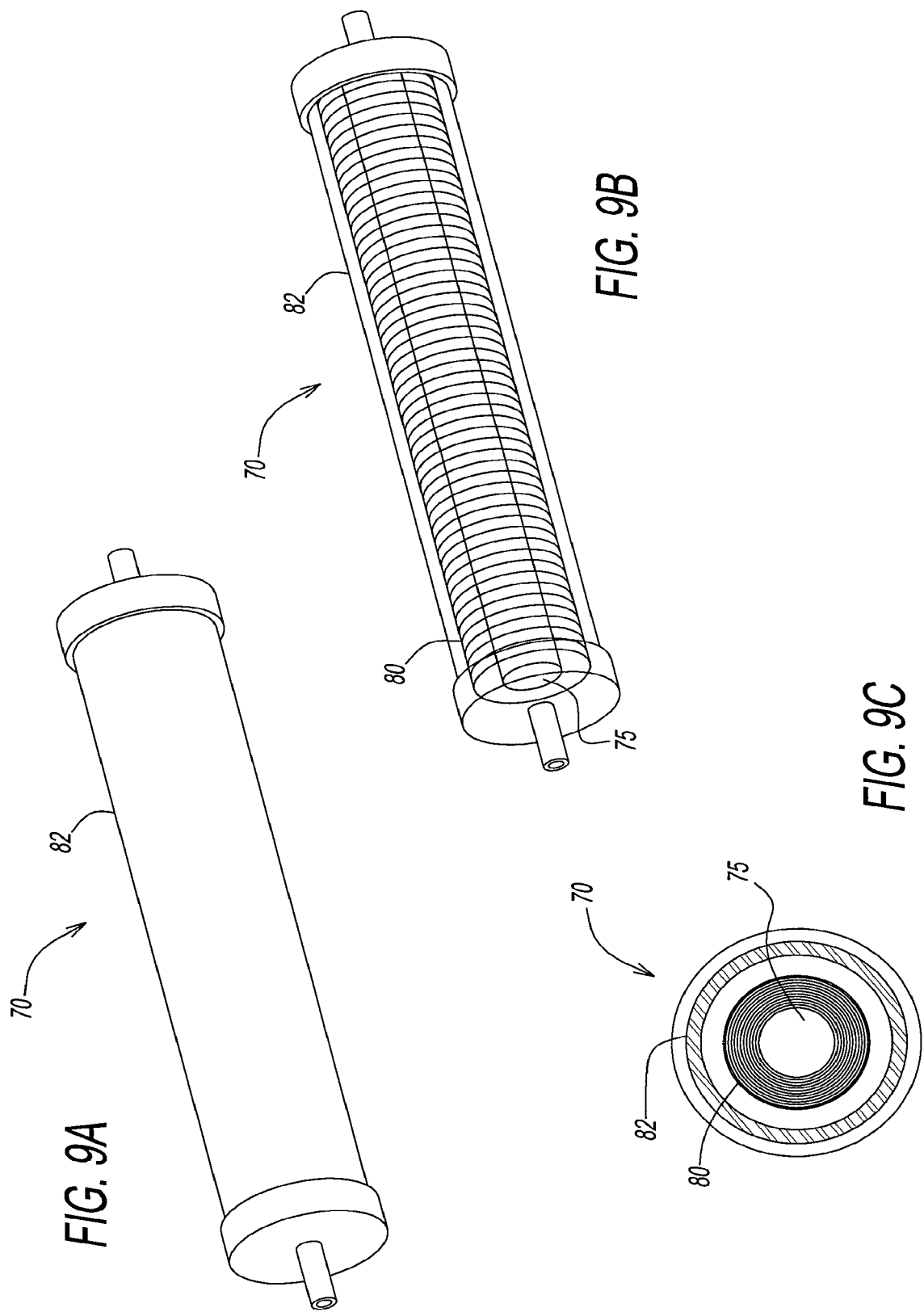

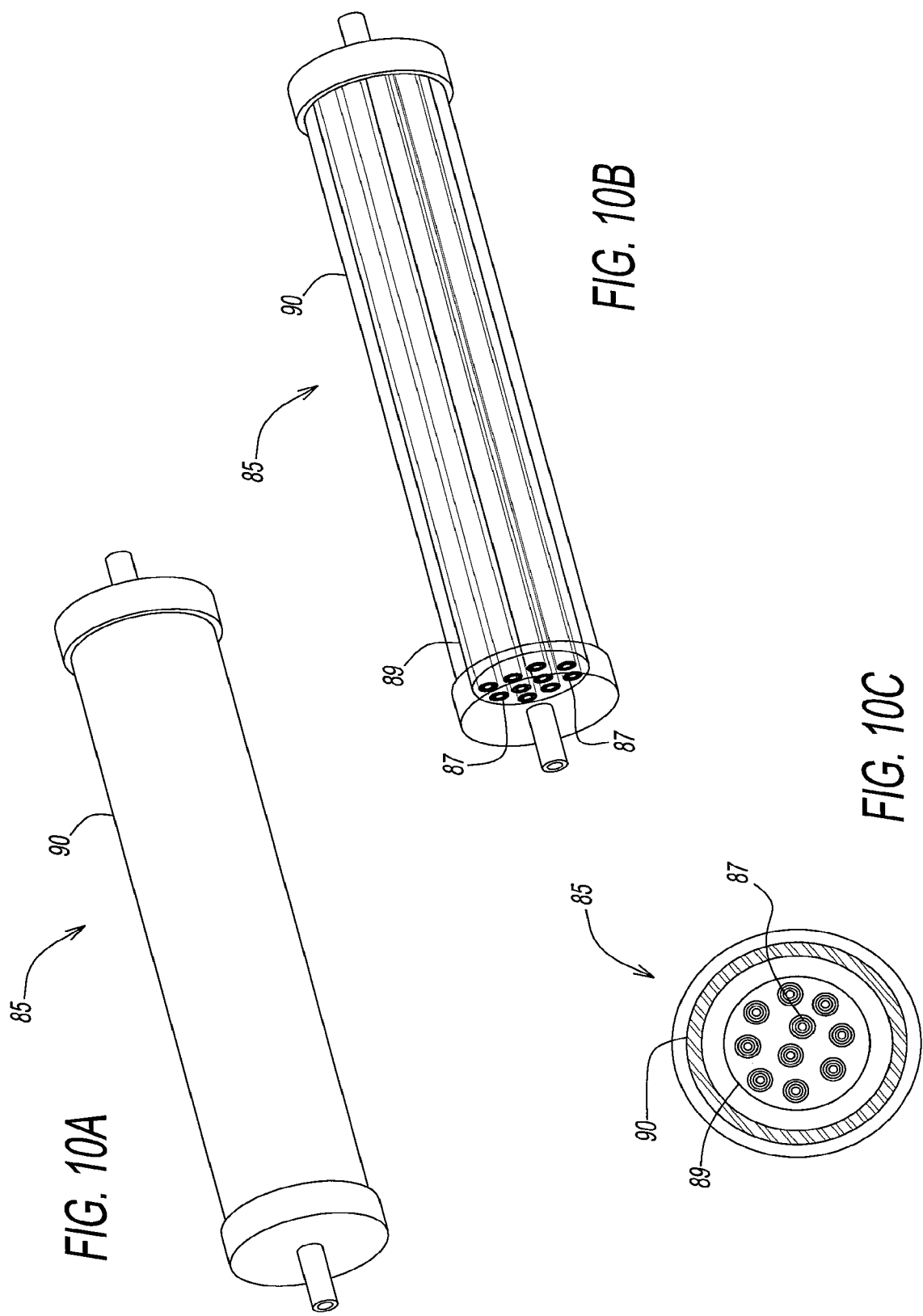

IRRADIATION OF RED BLOOD CELLS AND ANAEROBIC STORAGE

CROSS-REFERENCE TO RELATED APPLICATIONS

The present application is a continuation of U.S. patent application Ser. No. 16/156,136, filed Oct. 10, 2018, and now U.S. Pat. No. 11,284,616, issued Mar. 29, 2022, which is a continuation of U.S. patent application Ser. No. 13/289,722, filed Nov. 4, 2011, and now U.S. Pat. No. 10,136,635, issued Nov. 27, 2018, which is a non-provisional application of U.S. Provisional Application 61/410,684, filed Nov. 5, 2010. U.S. Patent application Ser. No. 13/289,722 is also a continuation-in-part of U.S. patent application Ser. No. 12/901,350, filed Oct. 8, 2010, and now U.S. Pat. No. 8,535,421, issued Sep. 17, 2013, which is a non-provisional application of U.S Provisional Application No. 61/331,693, filed May 5, 2010, and U.S Provisional Application No. 61/250,661, filed Oct. 12, 2009, the entireties of each of which are herein incorporated by reference.

BACKGROUND

1. Field

The present disclosure relates to a storage blood system having an oxygen/carbon dioxide depletion device and a blood storage bag for the long-term storage of red blood cells (RBCs). More particularly, the present disclosure relates to a blood storage system that is capable of removing oxygen and carbon dioxide from the red blood cells prior to storage and gamma and/or X-ray irradiating red blood cells either pre- or post-anaerobic treatment, as well as maintaining oxygen or oxygen and carbon dioxide depleted states during storage, thereby prolonging the storage life and minimizing deterioration of the deoxygenated red blood cells.

2. Background of the Art

Adequate blood supply and the storage thereof is a problem facing every major hospital and health organization around the world. Often, the amount of blood supply in storage is considerably smaller than the need therefore. This is especially true during crisis periods such as natural catastrophes, war and the like, when the blood supply is often perilously close to running out. It is at critical times such as these that the cry for more donations of fresh blood is often heard. However, unfortunately, even when there is no crisis period, the blood supply and that kept in storage must be constantly monitored and replenished, because stored blood does not maintain its viability for long.

Stored blood undergoes steady deterioration which is, in part, caused by hemoglobin oxidation and degradation and adenosine triphosphate (ATP) and 2-3,biphosphoglycerate (DPG) depletion. Oxygen causes hemoglobin (Hb) carried by the red blood cells (RBCs) to convert to met-Hb, the breakdown of which produces toxic products such as hemichrome, hemin and free $Fe^{3+}$. Together with the oxygen, these products catalyze the formation of hydroxyl radicals (OH$\cdot$), and both the OH$\cdot$ and the met-Hb breakdown products damage the red blood cell lipid membrane, the membrane skeleton, and the cell contents. As such, stored blood is considered unusable after 6 weeks, as determined by the relative inability of the red blood cells to survive in the circulation of the transfusion recipient. The depletion of DPG prevents adequate transport of oxygen to tissue thereby lowering the efficacy of transfusion immediately after administration (levels of DPG recover once in recipient after 8-48 hrs). In addition, these deleterious effects also result in reduced overall efficacy and increased side effects of transfusion therapy with stored blood before expiration date, when blood older than two weeks is used. Reduction in carbon dioxide content in stored blood has the beneficial effect of elevating DPG levels in red blood cells.

There is, therefore, a need to be able to deplete oxygen and carbon dioxide levels in red blood cells prior to storage on a long-term basis without the stored blood undergoing the harmful effects caused by the oxygen and hemoglobin interaction. Furthermore, there is a need to store oxygen and carbon dioxide depleted red blood cells in bags containing or in a bag surrounded by a barrier film with oxygen and carbon dioxide depletion materials. Furthermore, there is a need to optimize ATP and DPG levels in stored red blood cells by varying the depletion or scavenging constituents prior to and/or during storage depending upon the needs of the recipient upon transfusion. Furthermore, the blood storage devices and methods must be simple, inexpensive and capable of long-term storage of the blood supply.

Another issue relates to transfusion-associated graft-versus-host disease (TA-GVHD) which is a rare but nearly fatal complication associated with transfusion therapy in severely immuno-compromised blood recipients (for example, bone marrow transplant recipient, patients receiving aggressive chemotherapy, premature neonates). Prevention of TA-GVHD requires complete removal of, or arrest of the proliferative potential of T-lymphocytes from donor blood. Although leuko reduction filters are widely in use, they are not adequate in prevention of TA-GVHD because it cannot completely eliminate lymphocytes. Thus, lymphocyte inactivation by gamma-irradiation is currently the only recommended method for TA-GVHD prevention. Since it is a nearly fatal side effect of transfusion, some hospitals and countries irradiate every unit of RBC for TA-GVHD prevention. More commonly, RBC units ordered for specific recipients are irradiated before dispensed to the bedside.

Accordingly, anaerobically stored RBC must be compatible with gamma- or X-ray irradiation treatment so that anaerobically stored blood can be transfused to patients requiring irradiated RBC.

Gamma-irradiation abrogates proliferation of T-lymphocytes by damaging the DNA directly and via reactive oxygen species (ROS), namely hydroxyl radicals produced during gamma-radiolysis of water. Although red blood cells (RBC) do not contain DNA, ROS generated by gamma-irradiation have been shown to cause significant damage to the RBC. The major damage observed includes: i) increased hemolysis; ii) increased K+ leak; iii) reduction in post-transfusion survival; and iv) reduced deformability. Such damage is similar to, but an exaggerated form of storage-induced damage of RBC. The compromised status of RBC is well known to the physicians who administer such compromised RBC. The FDA mandates restricted use of such RBC in terms of shortened shelf life after gamma-irradiation (14 days) and/or 28 days total shelf life for irradiated units.

The irradiation of blood components has received increased attention due to increasing categories of patients eligible to receive such blood to prevent transfusion-associated graft versus host disease. However, irradiation leads to enhancement of storage lesions, which could have deleterious effects when such blood is transfused. It is well known in the field that the main deleterious side-effect of radiation on RBC is oxidative damage caused by ROS.

Radiation damage to RBC in the presence of oxygen can occur in two ways;
  i) By ROS generated during and immediately after irradiation. ROS can reside in RBC lipid, then attack proteins and lipids in vicinity later during storage, as well as to initiate peroxidation cycle of lipid and protein using oxygen to fuel.
  ii) Met-Hb and its denaturation products generated in i) above act as catalysts to further cause ROS-mediated oxidative damage during subsequent extended refrigerated storage of RBC. This is an enhanced version of storage lesion development using O2.

On the other hand, there is ample literature suggesting ROS as a major culprit in causing deterioration of red blood cell (RBC) during refrigerated storage at blood banks, and that storing RBC under anaerobic condition significantly reduce such damages. Studies have shown that irradiated red blood cells that are oxygen and oxygen and carbon dioxide depleted are equivalent or healthier (in terms of K+ leakage, hemolysis and oxidized proteins/lipids) in comparison to non-irradiated and non-oxygen and carbon dioxide depleted blood and non-oxygen and carbon dioxide depleted irradiated blood. In the context of the present application, the higher concentration of potassium in RBC storage media was at levels that indicated red blood cell damage. The present disclosure applies the finding of compatibility of gamma-irradiation with anaerobically stored blood, as well as the protective effects of anaerobic conditions in enhancing ATP, DPG and in reducing oxidative damage during refrigerated storage, to substantially reduce the negative or deleterious effect of gamma- and X-ray irradiation of RBCs in the presence of oxygen.

U.S. Pat. No. 5,362,442 to Kent describes adding a scavenger to bind free radicals such as ethanol. U.S. Patent No. 61875572 to Platz et al. describes adding chemical sensitizers; U.S. Pat. No. 6,482,585 to Dottori and U.S. Pat. No. 6,403,124, also to Dottori, describe adding L-carnitine or an alkanoul derivative to reduce RBC cell membrane damage induced by irradiation. These additives are not required to prevent the deleterious effects of irradiation on RBCs when treated anaeorobically.

SUMMARY

A method and system for gamma or X-ray irradiation of RBC under anaerobic or anaerobic and $CO_2$ depleted conditions, and extended refrigerated storage of such RBC under anaerobic or anaerobic and/or $CO_2$ depleted conditions using an oxygen and/or $CO_2$ depletion device.

A method and system for removing plasma with or without platelets, adding an additive solution (e.g., nutrient and/or metabolic supplements) to the concentrated RBC, filtering out leukocytes and/or platelets via a leuko reduction filter, removing oxygen and/or $CO_2$ from the filtered RBC, and gamma irradiating or X-ray irradiating the oxygen and/or $CO_2$ filtered RBC either prior to or during storage thereof. The preferred range of gamma irradiation is a minimum of between about 25 Gy to 50 Gy.

Gamma or X-ray irradiating RBC under anaerobic or anaerobic and $CO_2$ conditions (ambient to 1° C.) defined as less than 20% $SO_2$ (oxygen-saturation of hemoglobin), more preferably less than 5%, and most preferably less than 3%.

Storing gamma or X-ray irradiated (either under anaerobic or anaerobic and $CO_2$ conditions) RBC for extended time at 1-6° C. under anaerobic condition defined as less than 20% $SO_2$ (oxygen-saturation of hemoglobin), more preferably less than 5%, and most preferably less than 3%.

Gamma or x-ray irradiating RBC under anaerobic or anaerobic and $CO_2$ depleted conditions (ambient to 1° C.) defined as less than 20% $SO_2$ (oxygen-saturation of hemoglobin), more preferably $SO_2<5\%$, and most preferably $SO_2<3\%$ and $pCO_2<10$ mmHg; $pCO_2<5$ mmHg; $pCO_2<1$ mmHg.

Gamma or x-ray irradiating RBC under aerobic conditions (ambient to 1° C.) and then removing oxygen or oxygen and carbon dioxide from the irradiated RBC to levels defined as less than 20% $SO_2$ (oxygen-saturation of hemoglobin), more preferably $SO_2<5\%$, and most preferably $SO_2<3\%$ and $pCO_2<10$ mmHg; $pCO_2<5$ mmHg; $pCO_2<1$ mmHg. The gamma or x-ray irradiation under aerobic conditions and removal of oxygen or oxygen and carbon dioxide can be performed before placing blood for extended storage, or within 24 hr of blood collection, between 1 through 7 days after blood collection or beyond 7 days Using older blood, defined as blood stored for more than one week, and exposing such blood to gamma or x-ray irradiating RBC under aerobic conditions (ambient to 1° C.) and then removing oxygen or oxygen and carbon dioxide from the irradiated RBC to levels defined as less than 20% $SO_2$ (oxygen-saturation of hemoglobin), more preferably $SO_2<5\%$, and most preferably $SO_2<3\%$ and $pCO_2<10$ mmHg; $pCO_2<5$ mmHg; $pCO_2<1$ mmHg.

Using older blood, defined as blood stored for more than one week, and removing oxygen or oxygen and carbon dioxide from such older blood and exposing such blood to Gamma or x-ray irradiation at wherein the levels of oxygen and carbon dioxide are levels defined as less than 20% $SO_2$ (oxygen-saturation of hemoglobin), more preferably $SO_2<5\%$, and most preferably $SO_2<3\%$ and $pCO_2<10$ mmHg; $pCO_2<5$ mmHg; $pCO_2<1$ mmHg.

Storing gamma or X-ray irradiated or pre-irradiated RBC (either under anaerobic conditions with or without $CO_2$ depletion) RBC for extended time at 1-6° C. under anaerobic or anaerobic and $CO_2$ depleted condition defined as less than 20% $SO_2$ (oxygen-saturation of hemoglobin), more preferably less than 5%, and most preferably 3% and less than $pCO_2<10$ mmHg; $pCO_2<5$ mmHg; $pCO_2<1$ mmHg.

A preferred embodiment includes a blood storage system comprising: a collection vessel for red blood cells; an oxygen or oxygen/carbon dioxide depletion device; tubing connecting the collection vessel to the oxygen or oxygen/carbon dioxide depletion device and the storage vessel for red blood cells that can be gamma or X-ray irradiated and stored under anaerobic or anaerobic and $CO_2$ depleted condition for extended time.

Preferably, the anaerobic or anaerobic and $CO_2$ condition is measured as an oxygen-saturation of hemoglobin of less than 20% $SO_2$, preferably about 5% or less, and most preferably about 3% or less.

The oxygen or oxygen/carbon dioxide depletion device comprises: a cartridge; a plurality of gas permeable hollow fibers or sheets extending within the cartridge from an entrance to an exit thereof, wherein the hollow fibers or gas-permeable films are adapted to receiving and conveying red blood cells; and an amount of an oxygen scavenger or both oxygen scavenger and a carbon dioxide scavenger packed within the cartridge and contiguous to and in between the plurality of hollow fibers.

Preferably, the oxygen or oxygen/carbon dioxide depletion device comprises: a cartridge; a plurality of hollow fibers or gas-permeable films extending within the cartridge from an entrance to an exit thereof, wherein the hollow fibers or gas-permeable films are adapted to receiving and conveying red blood cells; and a low oxygen or a low oxygen and carbon dioxide environment is created outside the hollow fibers by flowing an inert gas in-between the hollow fibers.

The blood storage system further comprising a leuko reduction filter disposed between the collection vessel and the oxygen/carbon dioxide depletion device. The blood storage system further comprising an additive solution vessel in communication with the collection vessel. The blood storage system further comprising a plasma vessel in communication with the collection vessel.

A method for storing red blood cells, the method comprising: removing oxygen or oxygen and carbon dioxide from red blood cells to produce anaerobic red blood cells; and storing irradiated RBC with either gamma- or X-ray, thereby producing irradiated anaerobic red blood cells; and storing the irradiated anaerobic or anaerobic and $CO_2$ depleted red blood cells.

The irradiated anaerobic or irradiated anaerobic and $CO_2$ depleted red blood cells are preferably stored at a temperature from between about 1° C. to about 6° C. under anaerobic conditions.

The present disclosure also provides for a device and method of removing carbon dioxide ($CO_2$) in addition to oxygen ($O_2$) prior to or at the onset of anaerobic or anaerobic and $CO_2$ depleted storage and/or gamma or X-ray irradiation.

The present disclosure provides for a blood collection system that incorporates an oxygen or oxygen/carbon dioxide depletion device having an oxygen or oxygen and carbon dioxide sorbent in combination with a filter or membrane to strip oxygen or oxygen and carbon dioxide from the blood during transport to the storage bag, wherein the oxygen/carbon dioxide depleted blood is gamma or X-ray irradiated either prior to or during storage.

The present disclosure further provides for a system to deplete the oxygen or oxygen and carbon dioxide from collected red blood cells that includes an (optional additive solution), an oxygen or oxygen and carbon dioxide depletion device, and a blood storage bag that maintains the red blood cells in an oxygen or oxygen and carbon dioxide depleted state after gamma- or X-ray irradiation.

The present disclosure and its features and advantages will become more apparent from the following detailed description with reference to the accompanying drawings.

BRIEF DESCRIPTION OF THE DRAWINGS

FIGS. 8a through 8c illustrate another embodiment of a depletion device that depletes oxygen and carbon dioxide from red blood cell prior to storage.

FIGS. 9a through 9c illustrate another embodiment of a depletion device that depletes oxygen and carbon dioxide from red blood cells prior to storage wherein oxygen and $CO_2$ is scavenged by scavenger materials in the core of the cylinder, surrounded by hollow fibers.

FIGS. 10a through 10c illustrate another embodiment of a depletion device that depletes oxygen and carbon dioxide from red blood cells prior to storage wherein oxygen and $CO_2$ is scavenged by scavenger materials surrounding cylinders of hollow fibers enveloped in gas permeable, low water vapor transmission material.

DETAILED DESCRIPTION OF THE PREFERRED EMBODIMENT

RBCs do not require oxygen for their own survival. It was shown previously that when RBCs were stored in blood bank refrigerator (1-6° C.) under anaerobic or anaerobic and $CO_2$ depleted conditions, they demonstrated significantly improved post-transfusion recovery after 6-week storage compared to the conventionally stored controls. The mechanisms of reduction in storage lesions under anaerobic or anaerobic/$CO_2$ depleted conditions have been described and direct evidences demonstrated. It is, at least in part, due to reduction in oxidative damages in the presence of $O_2$ caused by ROS during refrigerated storage.

Because gamma- or X-ray irradiation exacerbate oxidative damage on treated RBC, storing irradiated RBC under anaerobic and, optionally, $CO_2$ depleted condition is not expected to intensify the damage; it is also expected to prevent damage resulting from ROS generated during irradiation by depriving $O_2$ that fuels those reactions.

Effectiveness of gamma- or X-ray irradiation is not dependent on the presence of oxygen. In contrast, anaerobic condition is shown to be more effective in causing damage to DNA (and thus inhibiting proliferation of lymphocytes). Furthermore, absence of $O_2$ during and/or immediately after gamma- or X-ray irradiation will reduce $O_2$-fueled oxidative damages to RBC induced by hydroxyl radicals and ROS produced by radiolysis of water with gamma- or X-rays.

Figure 1A:
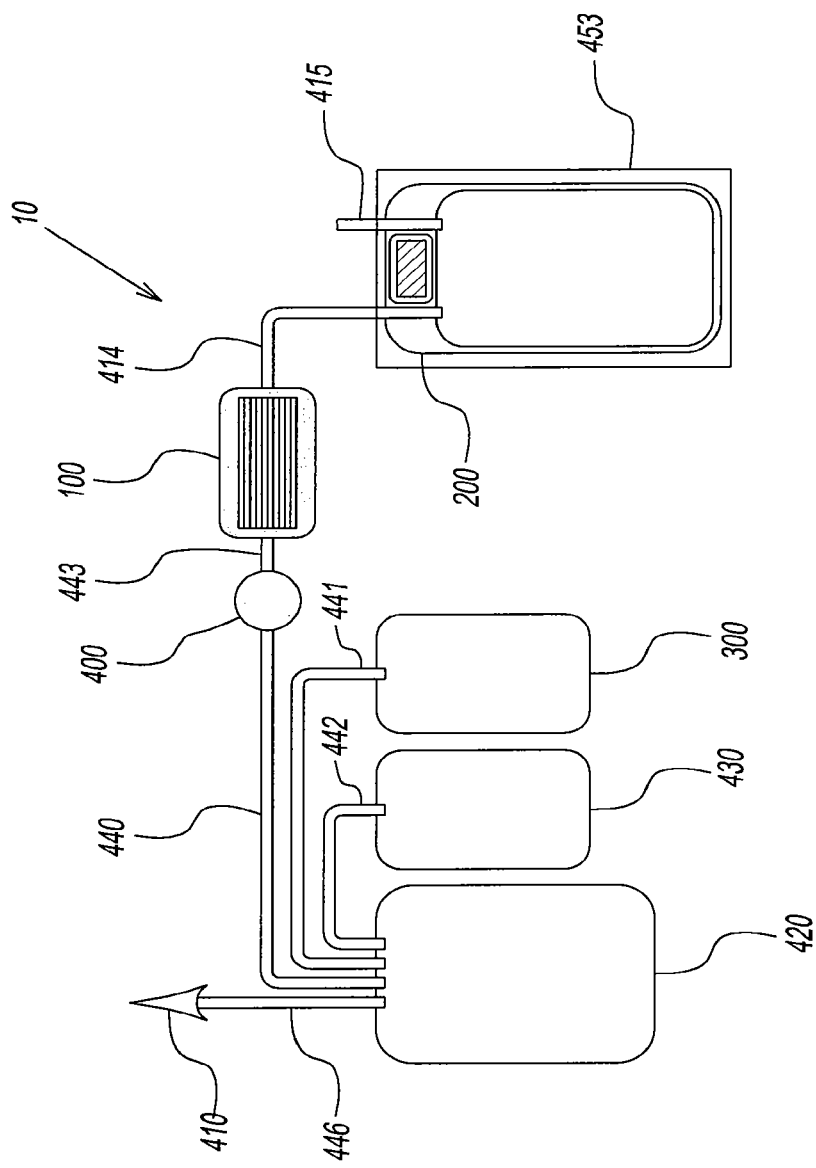
FIG. 1a illustrates the components of a gamma irradiated, disposable blood anaerobic storage system of the present disclosure.
Figure 1B:
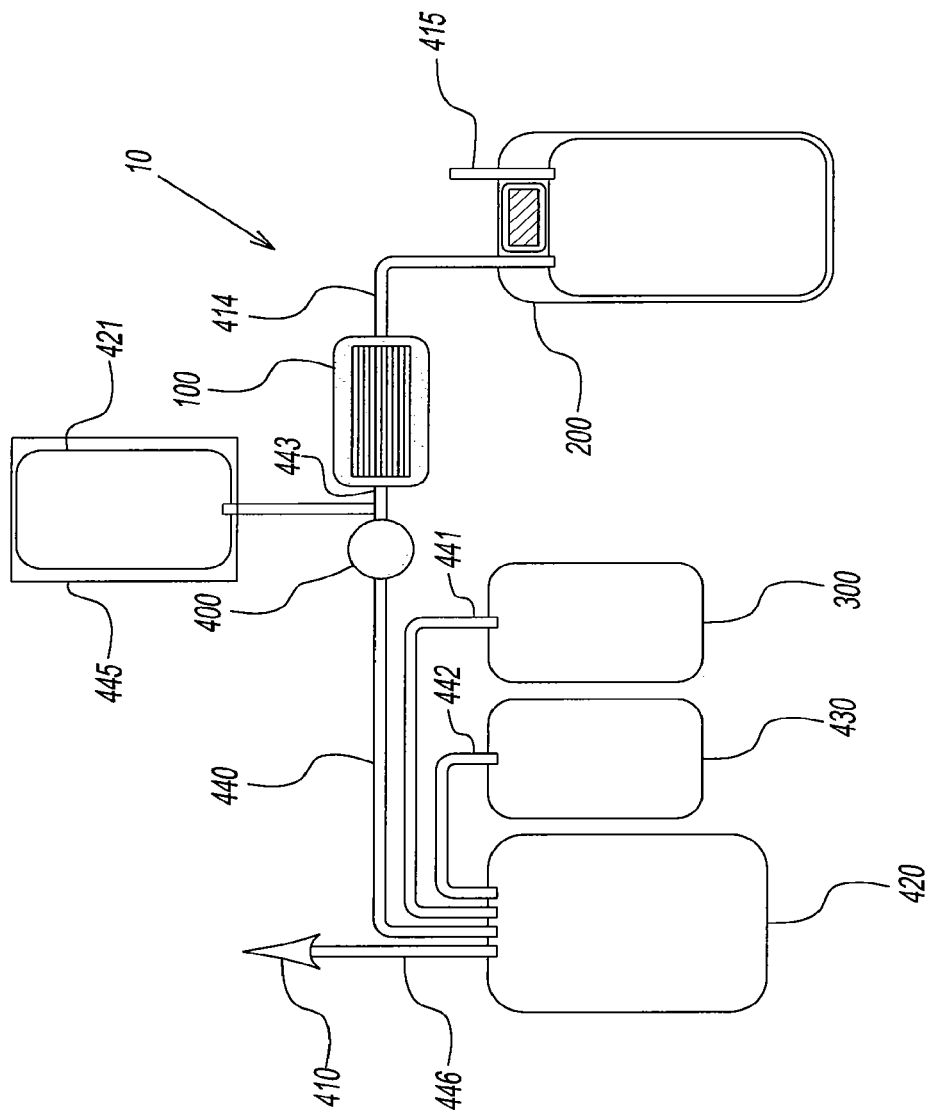
FIG. 1b illustrates the components of a second embodiment of a gamma irradiated, disposable blood anaerobic storage system of the present disclosure.

Referring to the drawings and in particular to FIG. 1a, a disposable blood anaerobic storage system is shown and referenced using reference numeral 10. The blood storage system includes an oxygen/carbon dioxide depletion device 100 (OCDD 100), an anaerobic blood storage bag 200 and an additive solution bag 300. OCDD 100 removes oxygen and/or carbon dioxide from red blood cells traveling through it. The system also contains a leuko reduction filter 400. Components conventionally associated with the process of blood collection are a phlebotomy needle 410, a blood collection bag 420 containing an anti-coagulant and a bag 430 containing plasma. Tubing can connect the various components of the blood storage system 10 in various configurations (one embodiment shown). Tube 440 connects collection bag 420 with leuko reduction filter 400. Tube 441 connects additive solution bag 300 with collection bag 420. Tube 442 connects plasma bag 430 with collection bag 420. Tube 443 connects leukoreduction filter 400 with OCDD 100. Tube 414 connects OCDD 100 with blood storage bag 200. Blood storage system 10 is preferably a single-use, disposable, low cost system. As filtered and oxygen or oxygen and carbon dioxide depleted blood passes from OCDD 100 to blood storage bag 200. Blood stored in bag 200 will be gamma and/or X-ray irradiated during storage via device 453. Bag 200 containing oxygen depleted or oxygen and carbon dioxide depleted RBC is placed into device 453 and exposed to gamma and/or X-ray radiation. Alternatively, pre-anaerobic blood stored in collection bag 421 can be gamma and/or X-ray irradiated via device 445 before passing through OCDD 100 and stored in bag 200, as shown in FIG. 1b. In FIG. 1b, bag 420 could also be gamma and/or X-ray irradiated in an irradiating device 445 prior to passing through leukoreduction filter 400.

Oxygen or oxygen/carbon dioxide depletion device 100 removes the oxygen from collected RBCs prior to the RBCs being stored in blood storage bag 200. The oxygen content in RBCs must be depleted from oxy-hemoglobin because more than 99% of such oxygen is hemoglobin-bound in venous blood. Preferably, the degree of oxygen saturation is to be reduced to less than 4% within 48 hours of blood collection. The oxygen depletion is preferably accomplished at room temperature. The affinity of oxygen to hemoglobin is highly dependent on the temperature, with a p50 of 26 mmHg at 37° C. dropping to ~4 mmHg at 4° C. Furthermore, this increase in $O_2$ affinity (Ka) is mainly due to reduction in $O_2$ release rate (k-off), resulting in an impractically low rate of oxygen removal once RBC is cooled to 4° C. Thus, it places a constraint on oxygen stripping such that it may be preferable to accomplish it before RBC are cooled to storage temperatures of 1° C. to 6° C.

In addition to oxygen depletion, carbon dioxide depletion has the beneficial effect of elevating DPG levels in red blood cells. Carbon dioxide exists inside RBCs and in plasma in equilibrium with $HCO_3^-$ ion (carbonic acid). Carbon dioxide is mainly dissolved in RBC/plasma mixture as carbonic acid and rapid equilibrium between $CO_2$ and carbonic acid is maintained by carbonic anhydrase inside RBC. Carbon dioxide is freely permeable through RBC membrane, while $HCO_3^-$ inside RBC and plasma is rapidly equilibrated by anion exchanger (band 3) protein. When $CO_2$ is removed from RBC suspension, it results in the known alkalization of RBC interior and suspending medium. This results from removal of $HCO_3^-$ inside and outside RBC; cytosolic $HCO_3^-$ is converted to $CO_2$ by carbonic anhydrase and removed, while plasma $HCO_3^-$ is removed via anion exchange inside RBC. Higher pH inside RBC is known to enhance the rate of glycolysis and thereby increasing ATP and DPG levels. ATP levels are higher in $Ar/CO_2$ (p<0.0001). DPG was maintained beyond 2 weeks in the Argon purged arm only (p<0.0001). Enhanced glycolysis rate is also predicted by dis-inhibition of key glycolytic enzymes via metabolic modulation and sequesterization of cytosolic-free DPG upon deoxygenation of hemoglobin as a result of anaerobic condition. DPG was lost at the same rate in both control and $Ar/CO_2$ arms (p=0.6) despite thorough deoxygenation of hemoglobin, while very high levels of ATP were achieved with OFAS3 additive (FIGS. 12a-12d).

Figure 2A:
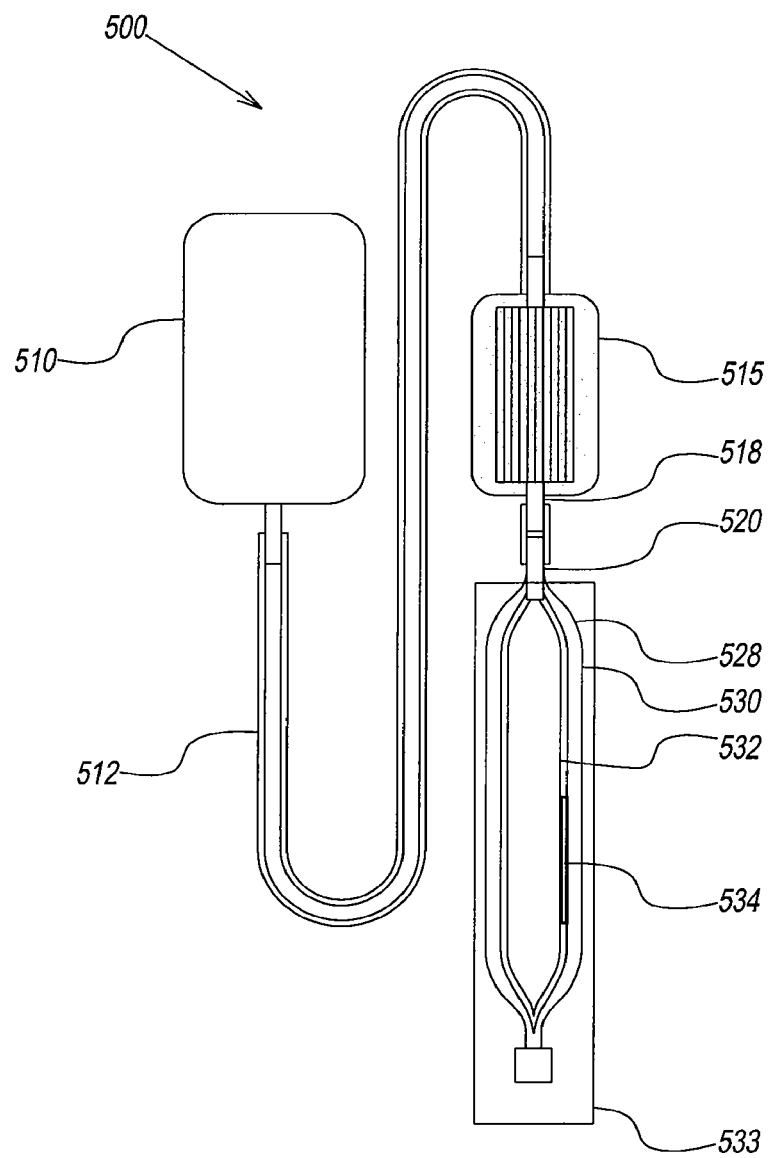
FIG. 2a illustrates the components of an embodiment of a disposable blood anaerobic storage system that are used in conjunction with RBC irradiation in which red blood cells are irradiated during anaerobic storage.

Referring to the drawings, and in particular to FIG. 2a, another embodiment of a disposable blood anaerobic storage system is shown and referenced using reference numeral 500. The anaerobic conversion system includes an oxygen or oxygen/carbon dioxide depletion device 515 (OCDD) and an anaerobic blood storage bag 528. OCDD 515 removes oxygen or oxygen and carbon dioxide from red blood cells traveling through it. Tubing connects the various components of the blood storage system 500. Tube 512 connects to RBC concentrate prepared by using an additive solution (e.g., AS1, AS3, AS5, SAGM, MAPS, etc.) and storing in bag 528 by passing aforementioned RBC concentrate from collection bag 510 through OCDD 515. Tubes 518 and 520 connect OCDD 515 with blood storage bag 528. Blood storage system 500 is preferably a single-use, disposable, low cost system. Oxygen and/or carbon dioxide depleted blood is gamma and/or X-ray in blood storage bag 528 via device 553 and subsequently stored for later transfusion.

Figure 2B:
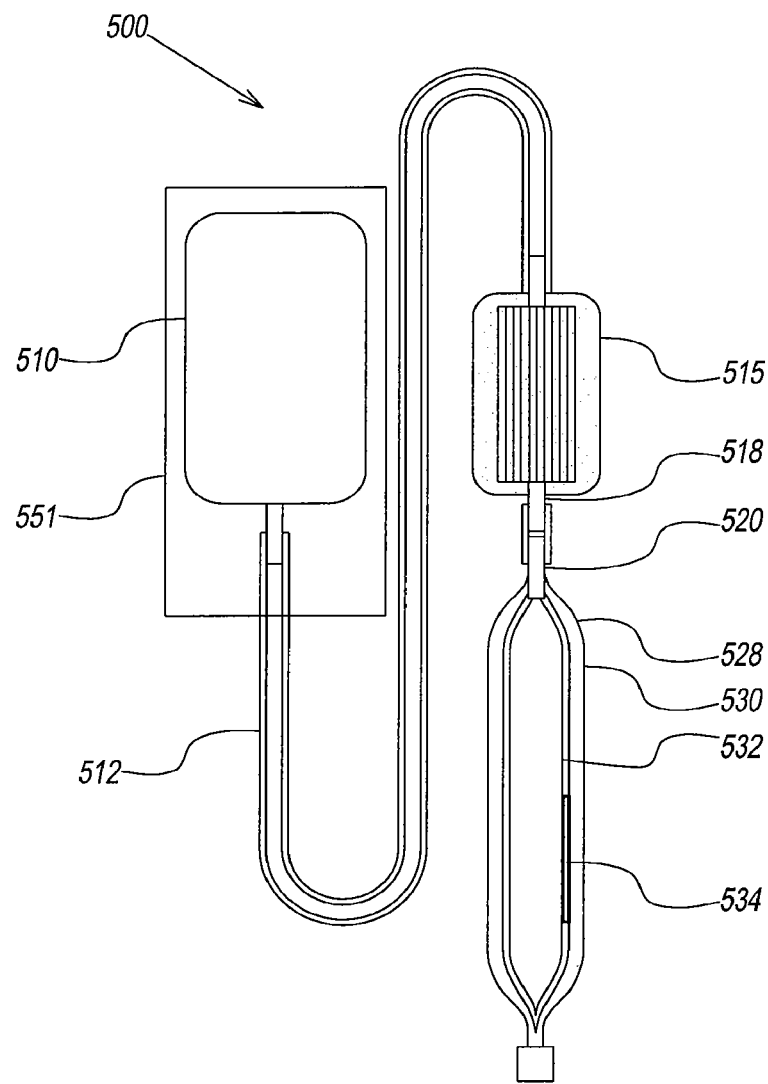
FIG. 2b illustrates the components of a second embodiment of a disposable blood anaerobic storage system that are used in conjunction with RBC irradiation.

Alternatively, blood in collection bag 510 may be gamma- or X-ray irradiated via device 551 prior to oxygen or oxygen and carbon dioxide depletion and low temperature storage, as shown in FIG. 2b. FIG. 2b applies to the scenario in which blood bag 510 contains older, for example 2 day old blood, that is then irradiated and depleted of oxygen or oxygen and or carbon dioxide, and stored.

Figure 3:
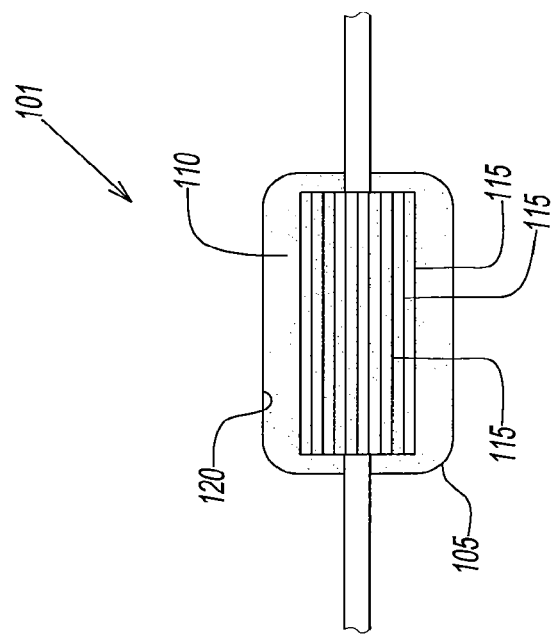
FIG. 3 illustrates a pre-storage oxygen/carbon dioxide depletion device of the present disclosure.

Referring to FIG. 3, an oxygen or oxygen/carbon dioxide depletion device (OCDD) 101 contains an oxygen sorbent 110. OCDD 101 is a disposable cartridge 105 containing oxygen sorbent 110 and a series of hollow fibers 115. Oxygen sorbent 110 is a mixture of non-toxic inorganic and/or organic salts and ferrous iron or other materials with high reactivity toward oxygen. Oxygen sorbent 110 is made from particles that have significant absorbing capacity for $O_2$ (more than 5 ml $O_2$/g) and can maintain the inside of cartridge 105 to less than 0.01% which corresponds to $PO_2$ less than 0.08 mmHg. Oxygen sorbent 110 is either free or contained in an oxygen permeable envelope. OCDD 101 of the present disclosure must deplete approximately 100 mL of oxygen from a unit of blood.

After oxygen and, optionally, carbon dioxide have been stripped from RBCs in the OCDD of FIG. 3, RBCs are stored in a blood storage bag 200. The oxygen content of RBC suspended in additive solution 300 must be reduced to equal to or less than 4% $SO_2$ before placing them in refrigerated storage. Further, oxygen depleted RBC must be kept in an anaerobic state and low carbon dioxide state throughout entire storage duration.

RBCs pass through an oxygen permeable film or membrane, that may be formed as hollow fibers 115 of FIG. 3.

The membrane or films may be constructed in a flat sheet or hollow fiber form. The oxygen permeable films can be non porous materials that are capable of high oxygen permeability rates (polyolefins, silicones, epoxies, polyesters, etc.) and oxygen permeable membranes are hydrophobic porous structures. These may be constructed of polymers (e.g., polyolefins, Teflon, PVDF, or polysulfone) or inorganic materials (e.g., ceramics). Oxygen depletion takes place as RBC pass through hollow fibers 115. Oxygen permeable films or oxygen permeable membranes may be extruded into sheets or hollow fibers 15. Accordingly, hollow fibers 115 and sheets may be used interchangeably. OCDD provides a simple structure having a large surface area to remove oxygen and maintain constant flow of blood therethrough. The oxygen depletion or removal is accomplished by irreversible reaction of ferrous ion in oxygen sorbent 110 with ambient oxygen to form ferric oxide. OCDD 101 does not need agitation for oxygen removal and can be manufactured easily to withstand centrifugation as part of a blood collection system as necessary.

Referring to FIGS. 7a through 7c and FIGS. 8a through 8c, examples of flushing depletion devices are disclosed. The depletion devices function to deplete, $O_2$ and $CO_2$, or $O_2$ alone, or $O_2$ with specific levels of $CO_2$ by supplying appropriate composition of flushing gas. Gases appropriate for depletion devices are, for example, Ar, He, $N_2$, Ar/$CO_2$, or $N_2$/$CO_2$.

FIGS. 9a through 9c and 10a through 910c, also disclose scavenging depletion devices. Depletion takes place with the use of scavengers or sorbents and without the use of external gases. In both types of depletion devices however, carbon dioxide depletion in conjunction with oxygen depletion is effective to enhance DPG and ATP, respectively, prior to storage in blood storage bags.

Figure 7B:
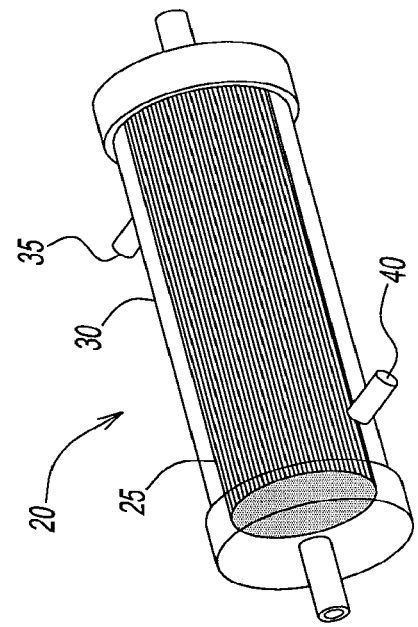
FIGS. 7a through 7c illustrate an embodiment of a depletion device that depletes oxygen and carbon dioxide from red blood cells prior to storage by a flushing inert gas or inert gas/$CO_2$ mixture of defined composition around a hollow fiber inside the assembly.
Figure 7C:
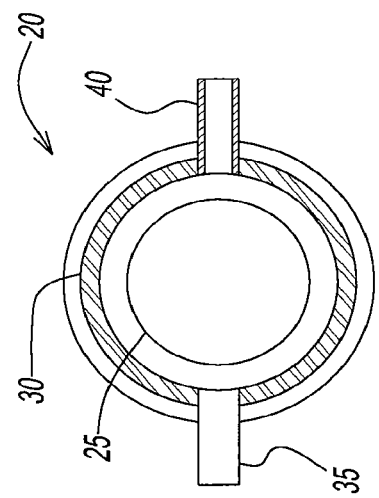
Figure 7A:
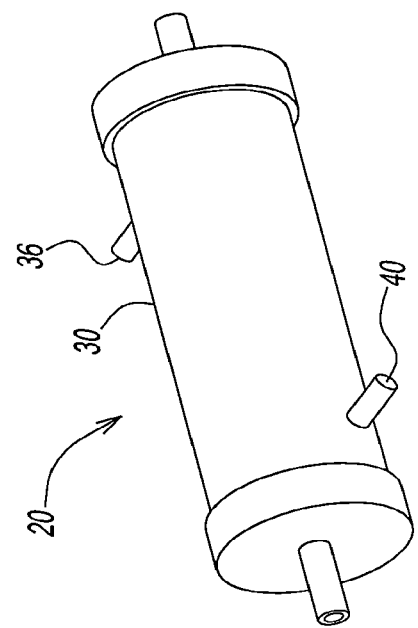

Referring to FIGS. 7a through 7c, a depletion device 20 is shown. Depletion device 20 includes a plurality of fibers 25, approximately 5000 in number, through which red blood cells flow. Plurality of fibers 25 are surrounded by a plastic cylinder 30. Plastic cylinder or cartridge 30 contains a gas inlet 35 and a gas outlet 40 through which a flushing gas or a combination of flushing gases, such as those mentioned above, are supplied to remove carbon and/or oxygen from blood. Specifications for depletion device 20 are shown in Table 1 below at second column.

TABLE 1

| Prototype Specification | External Gas Pathways | Externa Gas Pathways |
|---|---|---|
| Prototype Serial #: | Device 20 | Device 45 |
| Fiber Type: | Celgard 200/150-66FPI | Celgard 200/150-66FPI |
| Number of Fibers: | 5000 | 5000 |
| Active Length of Fibers (cm): | 13 | 28 |
| Fiber OD (microns): | 200 | 200 |
| Fiber ID (microns): | 150 | 150 |
| Total Length of Fibers | 15 | 30 |
| Active Fiber Surface Area (m2): | 0.4084 | 0.8796 |

Referring to FIGS. 8a through 8c, a depletion device 45 is shown. Depletion device 45, like device 20 of FIGS. 7a to 7c, includes a plurality of fibers 50, approximately 5000 in number, through which red blood cells flow. Plurality of fibers 50 are surrounded by a plastic cylinder 55. Plastic cylinder 55 contains a gas inlet 60 and a gas outlet 65 through which a gas or a combination of gases, such as those mentioned above are supplied to remove oxygen or oxygen and carbon dioxide from blood. Specifications for depletion device 45 are shown in Table 1 above in the third column. The active surface area of depletion of device 45 is twice that of device 20 because device 45 is twice as long as device 20.

FIGS. 9a through 9c disclose a depletion device 70 having a core 75 containing scavenging materials for either $O_2$, or both $O_2$ and $CO_2$. Core 75 is packed by a gas permeable film with very low liquid permeability. Hollow fibers 80 are wound around core 75, and a plastic cylinder 82 contains and envelopes hollow fibers 80. In this particular embodiment, the active surface area for depletion is approximately 0.8796 m² as shown in Table 2 below at the second column.

TABLE 2

| Prototype Specification | Center Core 125 grams Sorbent | 10 individual Bundles 200 grams Sorbent |
|---|---|---|
| Prototype Serial #: | Device 70 | Device 85 |
| Fiber Type: | Celgard 200/150-66FPI | Celgard 200/150-66FPI |
| Number of Fibers: | 5000 | 5000 |
| Active Length of Fibers (cm): | 13 | 28 |
| Fiber OD (microns): | 200 | 200 |
| Fiber ID (microns): | 150 | 150 |
| Total Length of Fibers | 15 | 30 |
| Active Fiber Surface Area (m2): | 0.8796 | 0.8796 |

FIGS. 10a through 10c disclose a depletion device 85 containing fiber bundles 87 enclosed in gas permeable film with very low liquid permeability. Fiber bundles 87 are surrounded by scavenger materials 89 for either $O_2$ or both $O_2$ and $CO_2$. Fiber bundles 87 and scavenger materials 89 are contained within a plastic cylinder 90. The active surface area for depletion is approximately 0.8796 m² as shown in Table 2 above at the third column.

Figure 11:
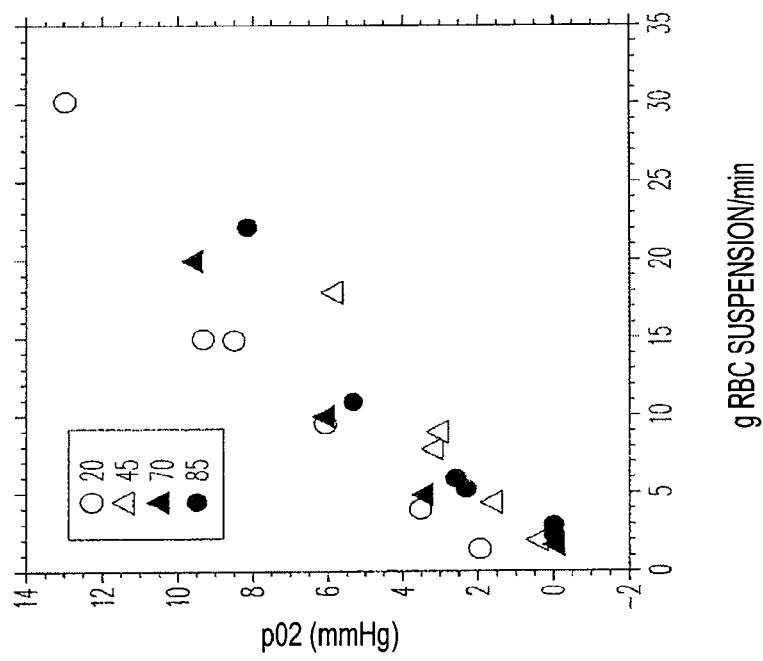
FIG. 11 illustrates a plot of flow rate of RBC suspension per minute versus oxygen partial pressure for the depletion devices of FIGS. 7a through 7c, FIGS. 8a through 8c, FIGS. 9a through 9c and FIGS. 10a through 10c.

FIG. 11 is a plot of the performance of flushing depletion devices 20 and 45 and scavenging depletion devices 70 and 85. The data of FIG. 11 was plotted using the following conditions: Hematocrit, 62% (pooled 3 units of pRBC), and 21° C. at various head heights to produce different flow rates. Oxygen/carbon dioxide scavenger (Multisorb Technologies, Buffalo, NY) was activated with adding 5% and 12% w/w water vapor for device 79 and device 85, respectively. Data are plotted with flow rate (g RBC suspension per min) vs. $pO_2$ (mmHg).

In the oxygen/carbon dioxide depletion devices disclosed herein, a plurality of gas permeable films/membranes may be substituted for the plurality of hollow fibers. The films and fibers may be packed in any suitable configuration within the cartridge, such as linear or longitudinal, spiral, or coil, so long as they can receive and convey red blood cells.

FIG. 11 shows that lowest oxygen saturation is achieved using devices 45 and 85. Device 45 exhibits a larger active surface area exposed to gases along length of fibers 50. Device 85 also has a long surface area of exposure to scavenging materials. Device 85 has bundles 87 surrounded by scavenging materials 89. The space occupied by scavenging materials 89 between bundles 87 promotes dispersion of oxygen and carbon dioxide from red blood cells contained in fiber bundles 87, thus aiding scavenging of oxygen and carbon dioxide from red blood cells.

A further use of the depletion devices is to add back oxygen and or carbon dioxide prior to transfusion by flushing with pure oxygen or air. This use is for special cases, such as massive transfusions, where the capacity of the lung to re-oxygenate transfused blood is not adequate, or sickle cell anemia.

Similarly, depletion devices can be used to obtain intermediate levels or states of depletion of oxygen and carbon dioxide depending needs of the patient to obtain optimal levels in the transfused blood depending upon the patients needs.

Figure 4:
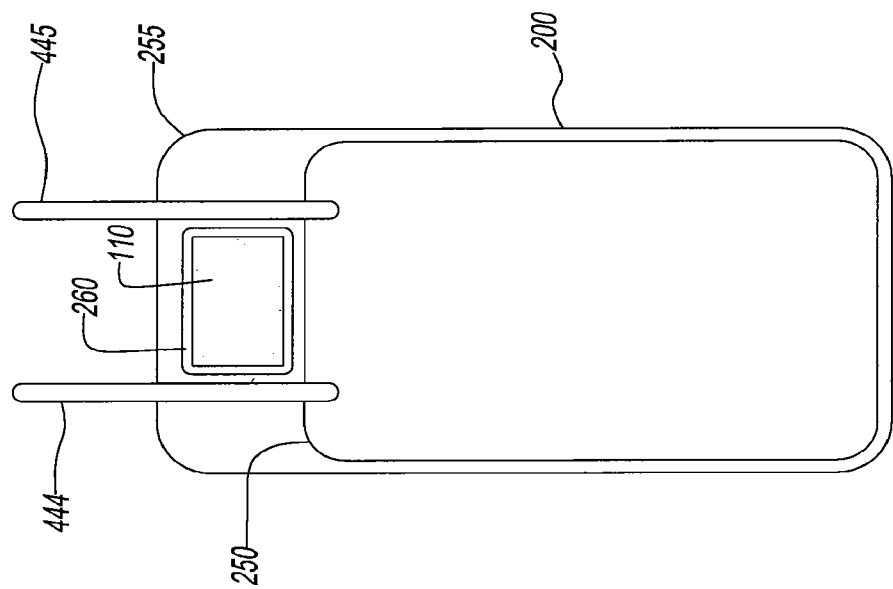
FIG. 4 illustrates a first embodiment of a blood storage bag having a storage bag with a secondary outer oxygen film containing an oxygen sorbent in a pocket.

Referring to FIG. 4, a blood storage bag 200 according to a preferred embodiment of the present disclosure is provided. Blood bag 200 has an inner blood-compatible bag 250 (preferably polyvinyl chloride (PVC)), and an outer barrier film bag 255. The material of bag 250 is compatible with RBCs. Disposed between inner bag 250 and outer oxygen barrier film bag 255 is a pocket that contains an oxygen/carbon dioxide sorbent 110. Barrier film bag 255 is laminated to the entire surface of inner bag 250. Sorbent 110 is contained in a sachet 260, which is alternately referred to as a pouch or pocket. Sorbent 110 is optimally located between tubing 440 that leads into and from bag 200, specifically between inner bag and outer oxygen barrier film bag 255. This location will ensure that oxygen disposed between these two bags will be scavenged or absorbed. Oxygen sorbent is ideally located in a pouch or pocket 260 and not in contact with RBCs. Oxygen sorbent may also be combined with $CO_2$ scavengers or sorbents, enabling sorbent 110 to deplete both oxygen and carbon dioxide at the same time.

Figure 5B:
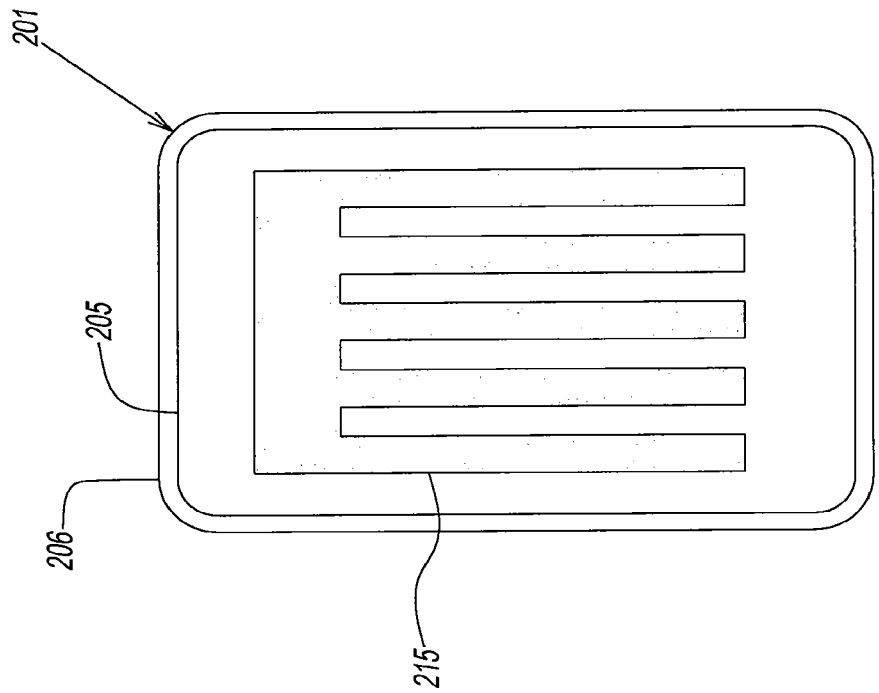
FIG. 5b illustrates a third embodiment of a blood storage bag having a storage bag a laminated oxygen film barrier with a large sorbent in contact with the RBCs.
Figure 5A:
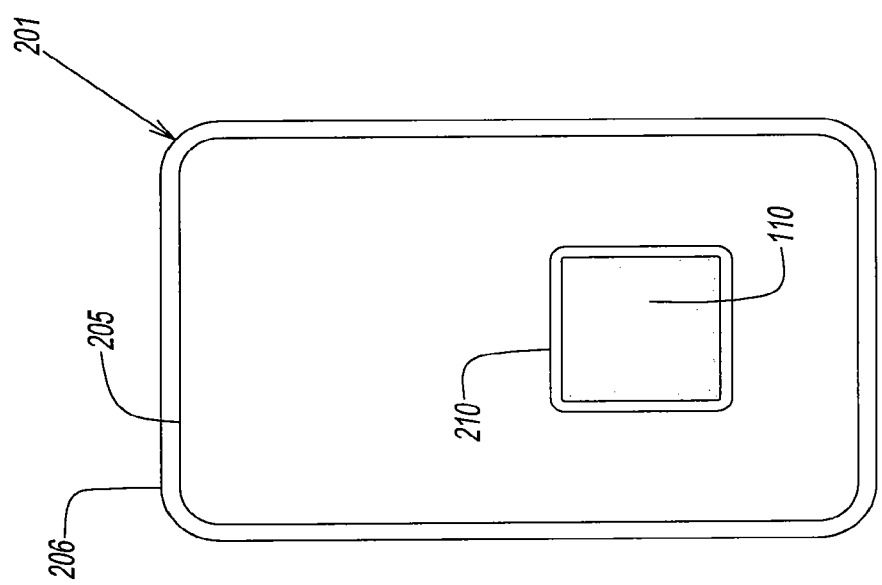
FIG. 5a illustrates a pre-storage oxygen/carbon dioxide depletion bag having a blood storage bag with a large sorbent sachet enclosed in gas-permeable, red blood cell compatible polymers in contact with the RBCs.

Referring to FIGS. 5a and 5b, blood storage bags 201 and 202 are configured to store RBCs for extended storage periods of time. Inner blood storage bags 205 are preferably made from DEHP-plasticized PVC and are in contact with RBCs. DEHP-plasticized PVC is approximately 200 fold less permeable to oxygen compared to silicone. However, PVC is insufficient as an oxygen barrier to maintain the anaerobic state of RBCs throughout the storage duration. Therefore, blood storage bags 201 and 202 are fabricated with outer transparent oxygen barrier film 206 (e.g., nylon polymer) laminated to the outer surface inner blood bag 205. This approach, as well as one shown in FIG. 3, uses accepted PVC for blood contact surface (supplying DEHP for cell stabilization) at the same time prevents oxygen entry into the bag during extended storage.

In FIG. 5a, a small sachet 210 containing oxygen/carbon dioxide sorbent 110 enveloped in oxygen-permeable, RBC compatible membrane is enclosed inside of laminated PVC bag 205 and in contact with RBCs. Small sachet envelope 210 is preferably made from a silicone or siloxane material with high oxygen permeability of biocompatible material. Sachet envelope 210 has a wall thickness of less than 0.13 mm thickness ensures that $O_2$ permeability ceases to become the rate-limiting step. PVC bag 205 may also contain carbon dioxide scavengers.

Referring to FIG. 5b, bag 202 has a similar configuration to bag 201 of FIG. 4a. However, bag 202 has a large sorbent 215 enclosed inside of PVC bag 205. Large sorbent 215 preferably has a comb-like configuration to rapidly absorb oxygen during extended storage. The benefit of laminated bags of FIGS. 4a and 4b is that once RBCs are anaerobically stored in bags, no further special handling is required. Similarly, bag 202 may contain carbon dioxide scavenger to provide carbon dioxide-scavenging in addition to oxygen-scavenging capability.

Figure 6B:
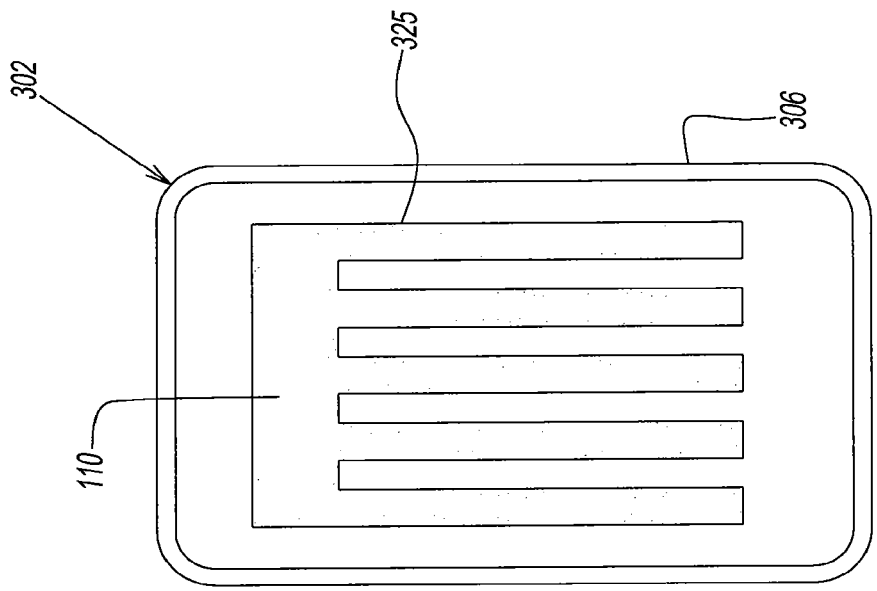
FIG. 6b illustrates a fifth embodiment of a blood storage bag having a secondary outer barrier bag surrounding an inner blood storage bag having a large oxygen sorbent sachet enclosed in a gas permeable, red blood cell compatible polymers in contact with RBCs.
Figure 6A:
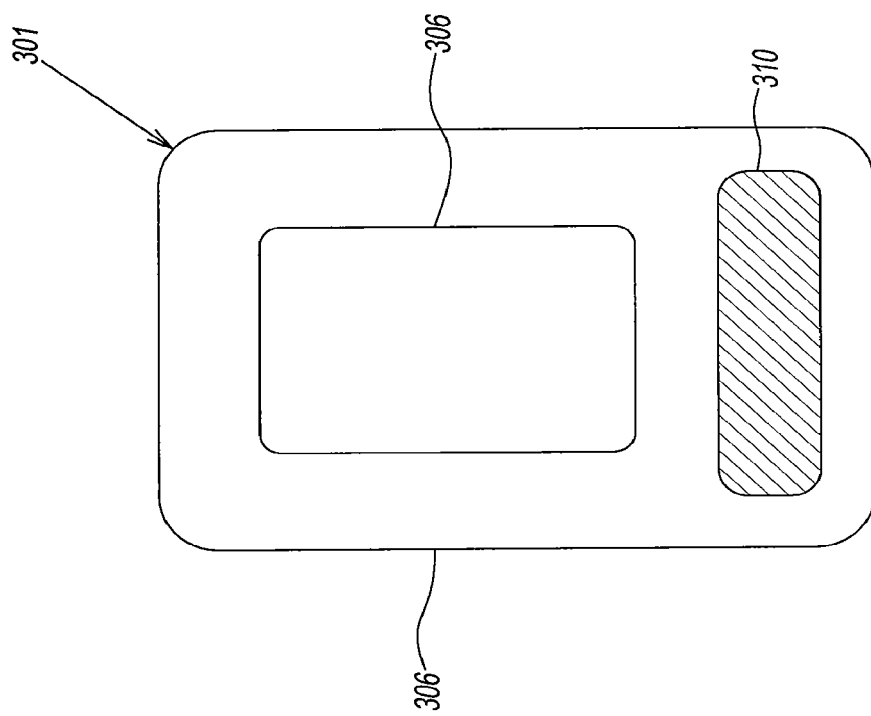
FIG. 6a illustrates a fourth embodiment of a blood storage bag having a secondary configured secondary outer barrier bag surrounding an inner blood storage bag having an oxygen sorbent.

Referring to the embodiments of FIGS. 6a and 6b, RBCs are stored in secondary bags 301 and 302, respectively, in order to maintain an anaerobic storage environment for RBC storage. Secondary bags 301 and 302 are transparent oxygen barrier films (e.g., nylon polymer) that compensate for the inability of PVC blood bags 305 and 320, respectively, to operate as a sufficient oxygen barrier to maintain RBCs in an anaerobic state. Secondary bags 301 and 302 are made with an oxygen barrier film, preferably a nylon polymer or other transparent, flexible film with low oxygen permeability.

Referring to FIG. 6a, a small oxygen/carbon dioxide sorbent 310 is disposed between a PVC barrier bag 305 and secondary bag 306 to remove slowly diffusing oxygen. FIG. 6a is similar to the preferred embodiment of the blood bag of FIG. 4 except that secondary bag 306 is separate from and not bonded to bag 305 in this embodiment. PVC bag 305 including ports are enclosed in secondary barrier bag 305. Oxygen sorbent 310 may optionally contain carbon dioxide scavengers to provide both oxygen and carbon dioxide scavenging capability.

Referring to FIG. 6b, a secondary bag 302 contains a large sachet 325 inside of PVC bag 320. Sachet 325 is filled with either oxygen or oxygen/carbon dioxide sorbent 110. Sachet 325 is a molded element with surface texture to increase the surface area. Sachet 325 has a comb-like geometry for rapid oxygen or oxygen/carbon dioxide depletion. Sachet 325 acts rapidly to strip oxygen or oxygen/carbon dioxide from RBCs prior to refrigeration and storage of RBCs in place of OCDD of FIG. 3. However, with this configuration, agitation is necessary, therefore sachet 325 must possess a large surface area, high oxygen or oxygen/carbon dioxide permeability and mechanical strength to withstand centrifugation step during component preparation and the prolonged storage. Sachet 325 is preferably made from materials such as 0.15 mm thick silicone membrane with surface texture to increase the surface area. Sachet 325 may be made from materials such as PTFE or other fluoropolymer. Sachet 325 may have a rectangular shape such, such as, for example, a 4"×6" rectangle, although other sizes are possible, for the anaerobic maintenance. Sachet 325 may contain carbon dioxide scavengers in addition to oxygen scavengers to provide oxygen and carbon dioxide scavenging capability.

The embodiments of FIGS. 6a and 6b are easily made from off-shelf components except for sachet 325 of FIG. 6b. In order to access RBCs for any testing, secondary bags 301 and 302 must be opened. Unless the unit is transfused within short time, RBC must be re-sealed with fresh sorbent for further storage. (1 day air exposure of storage bag would not oxygenate blood to appreciable degree, since PVC plasticized with DEHP has relatively low permeability to oxygen).

In FIGS. 5a, 5b, 6a and 6b, the PVC bag is preferably formed with the oxygen barrier film, such as a $SiO_2$ layer formed with the sol-gel method. A portion of the sheet material will be sealed on standard heat sealing equipment, such as radiofrequency sealers. Materials options may be obtained in extruded sheets and each tested for oxygen barrier, lamination integrity, and seal strength/integrity.

For each of the several embodiments addressed above, an additive solution from bag 300 is provided prior to stripping oxygen and carbon dioxide from the RBCs is used. The additive solution 300 preferably contains the following composition adenine 2 mmol/L; glucose 110 mmol/L; mannitol 55 mmol/L; NaCl 26 mmol/L; $Na_2HPO_4$ 12 mmol/L citric acid and a pH of 6.5. Additive solution 300 is preferably an acidic additive solution OFAS3, although other similar additive solutions could also be used that are shown to enhance oxygen/carbon dioxide-depleted storage. OFAS3 has shown enhanced ATP levels and good in vivo recovery as disclosed herein. While OFAS3 is a preferred additive solution, other solutions that offer similar functionality could also be used. Alternatively, additive solutions used currently in the field, such as AS1, AS3, AS5, SAGM, and MAPS can also be used. Additive solutions help to prevent rapid deterioration of RBCs during storage and are typically added prior to RBCs being made anaerobic.

Additionally, we envision that the OCDD and storage bags 100 and 200 can be manufactured independent of other components of the disposable, anaerobic blood storage system (i.e., every item upstream of and including leuko reduction filter 400 in FIG. 1*a*).

It is within the scope of the present disclosure to remove oxygen from the RBCs or to strip oxygen and carbon dioxide from the blood prior to storage in the storage bags. An oxygen scavenger can be used to remove the oxygen from the RBCs prior to storage in the blood bags. As used herein, "oxygen scavenger" is a material that irreversibly binds to or combines with oxygen under the conditions of use. For example, the oxygen can chemically react with some component of the material and be converted into another compound. Any material where the off-rate of bound oxygen is zero can serve as an oxygen scavenger. Examples of oxygen scavengers include iron powders and organic compounds. The term "oxygen sorbent" may be used interchangeably herein with oxygen scavenger. As used herein, "carbon dioxide scavenger" is a material that irreversibly binds to or combines with carbon dioxide under the conditions of use. For example, the carbon dioxide can chemically react with some component of the material and be converted into another compound. Any material where the off-rate of bound carbon dioxide is zero can serve as a carbon dioxide scavenger. The term "carbon dioxide sorbent" may be used interchangeably herein with carbon dioxide scavenger. For example, oxygen scavengers and carbon dioxide scavengers are provided by Multisorb Technologies (Buffalo, NY) or Mitsubishi Gas Chemical Co (Tokyo, Japan). Oxygen scavengers may exhibit a secondary functionality of carbon dioxide scavenging. Such materials can be blended to a desired ratio to achieve desired results.

Carbon dioxide scavengers include metal oxides and metal hydroxides. Metal oxides react with water to produce metal hydroxides. The metal hydroxide reacts with carbon dioxide to form water and a metal carbonate. For example, if calcium oxide is used, the calcium oxide will react with water that is added to the sorbent to produce calcium hydroxide

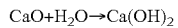

$CaO + H_2O \rightarrow Ca(OH)_2$

The calcium hydroxide will react with carbon dioxide to form calcium carbonate and water.

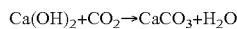

$Ca(OH)_2 + CO_2 \rightarrow CaCO_3 + H_2O$

It will be appreciated that scavengers can be incorporated into storage receptacles and bags in any known form, such as in sachets, patches, coatings, pockets, and packets.

If oxygen removal is completed prior to introduction of the RBCs to the blood storage device, then it can be accomplished by any method known in the art. For example, a suspension of RBCs can be repeatedly flushed with an inert gas (with or without a defined concentration of carbon dioxide), with or without gentle mixing, until the desired oxygen and or carbon dioxide content is reached or until substantially all of the oxygen and carbon dioxide has been removed. The inert gas can be argon, helium, nitrogen, mixtures thereof, or any other gas that does not bind to the hememoiety of hemoglobin.

The OCDDs and various storage bags of the present disclosure can be used in varying combinations. For example, OCDD 101 of FIG. 3 can be used with blood bag of FIG. 4, 201 of FIG. 5*a* or 301 of FIG. 6*a*. When oxygen is depleted by in-bag sachet 215 of FIG. 6*b*, it can be stored as in FIG. 6*b* or oxygen/carbon dioxide-depleted content transferred to the final storage bag such as FIG. 4, FIG. 5*a* or FIG. 6*a* for extended storage. Other combinations and configurations are fully within the scope of the present disclosure.

The present disclosure also provides another embodiment of a blood storage device. The device is a sealed receptacle adapted to retain and store red blood cells. The receptacle has walls formed from a laminate. The laminate has (a) an outer layer of a material substantially impermeable to oxygen or oxygen and carbon dioxide, (b) an inner layer of a material compatible with red blood cells, and (c) an interstitial layer between the outer layer and the inner layer. The interstitial layer is of a material having admixed therein an amount of an oxygen scavenger or an oxygen/carbon dioxide scavenger. The layers preferably take the form of polymers. A preferred polymer for the outer layer is nylon. A preferred polymer for inner layer is PVC. The polymer of the interstitial layer should provide effective adhesion between the inner and outer layers and provide effective admixture of oxygen scavengers or oxygen/carbon dioxide scavengers therein. Useful polymers for the interstitial layer include, for example, olefin polymers, such as ethylene and propylene homopolymers and copolymers, and acrylic polymers.

The present disclosure also provides another embodiment of a blood storage system. The system has a collection bag for red blood cells; a unitary device for depleting oxygen or oxygen and carbon dioxide and reducing leukocytes and/or platelets from red blood cells; a storage bag for red blood cells; and tubing connecting the collection bag to the unitary device and the unitary device to the storage bag. A feature of this embodiment is that the functions of depleting oxygen or oxygen and carbon dioxide and reducing leukocytes and/or platelets from red blood cells are combined into a single, unitary device rather than require separate devices. For instance, unitary device can take the form of a single cartridge. Leukocyte and/or platelet reduction is typically carried out by passing red blood cells through a mesh. In this embodiment, a mesh can be incorporated into either the flushing or the scavenging oxygen or oxygen/carbon dioxide depletion device disclosed herein. The mesh is preferably located within the device so that leukocyte and/or platelet reduction takes place prior to the onset of flushing or scavenging.

The following are examples of the present disclosure and are not to be construed as limiting.

EXAMPLES

FIGS. 12*a* through 12*h* show the results of a 3-arm study showing: a control (aerobic OFAS3 with no $O_2$ or $CO_2$ depletion), anaerobic OFAS3 (both $O_2$ and $CO_2$ depleted with pure Ar), and $O_2$ only depleted with 95% Ar and 5% $CO_2$ ($CO_2$ is not depleted).

Whole blood was collected into CP2D (Pall), centrifuged 2K×G for 3 minutes, plasma removed, and additive solution AS-3 (Nutricel, Pall), or experimental OFAS3 added. The unit was evenly divided into 3 600 mL bags. 2 bags were gas exchanged ×7 with Ar or Ar/CO$_2$, transferred to 150 mL PVC bags and stored 1° C. to 6° C. in anaerobic cylinders with Ar/H$_2$ or Ar/H$_2$/CO$_2$. One control bag was treated in the same manner without a gas exchange and stored 1° C. to 6° C. in ambient air. Bags were sampled weekly for up to 9 weeks.

The plots of FIGS. 12a, 12c, 12e and 12g: use the additive solution OFAS3 (200 mL; experimental, proprietary) and the plots of FIGS. 12b, 12d, 12f and 12h, use the AS-3 additive solution. Comparing additive solutions, effects of CO$_2$ depletion on DPG levels were similar. OFAS3 showed higher ATP when oxygen was depleted (±CO$_2$), and O$_2$ depletion alone showed significant enhancement of ATP compared to aerobic control. AS-3 additive exhibited no significant enhancement of ATP when O$_2$ alone was depleted.

Figure 12B:
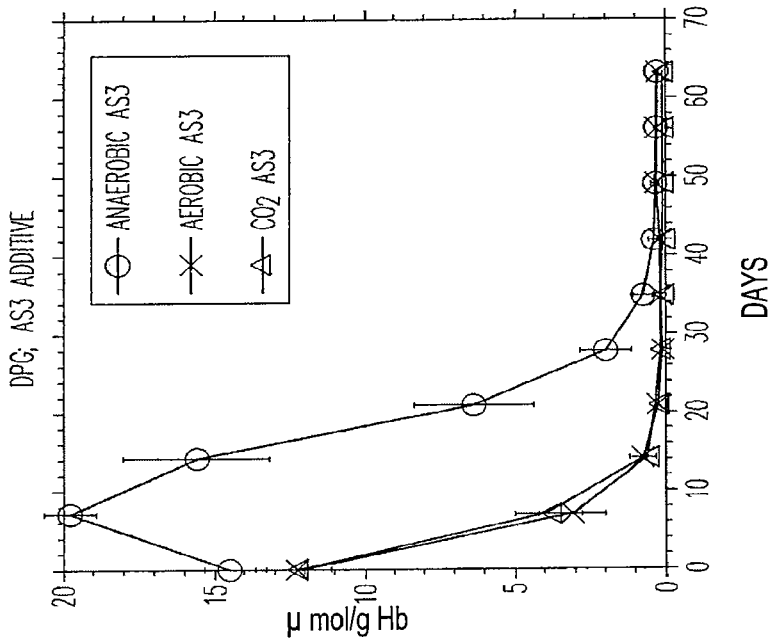
FIGS. 12a through 12h illustrate plots of the effect of oxygen and oxygen and carbon dioxide depletion on metabolic status of red blood cells during refrigerated storage.
Figure 12A:
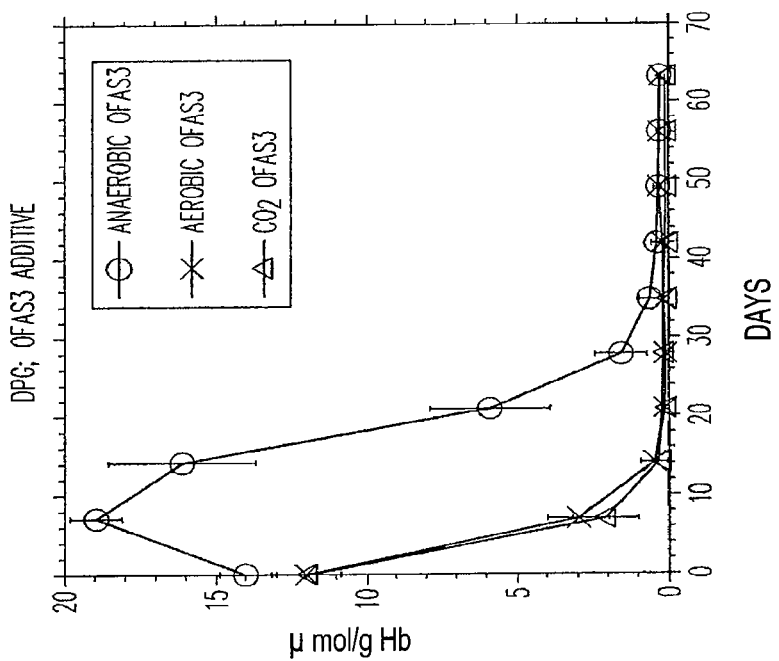

FIGS. 12a and 12b: DPG levels during storage. DPG levels were maintained for over 2 weeks, when CO$_2$ was removed in addition to oxygen.

Figure 12D:
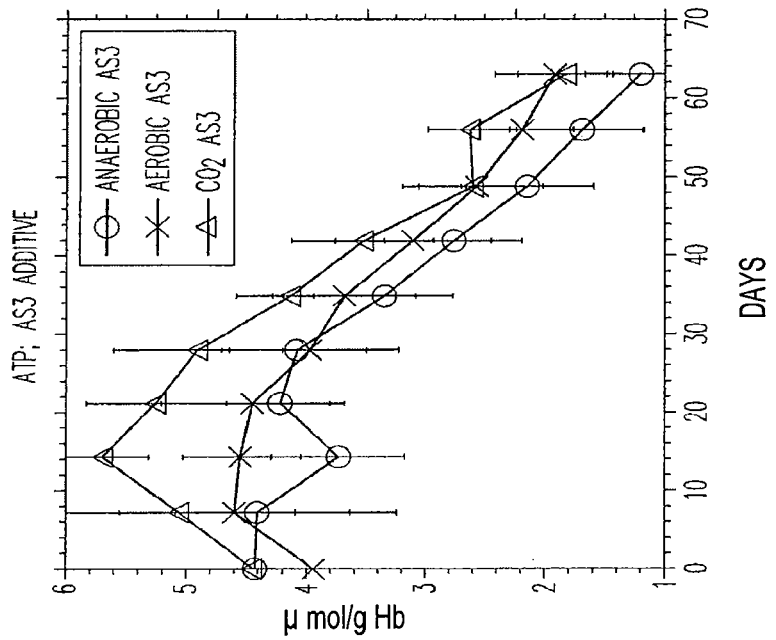
Figure 12C:
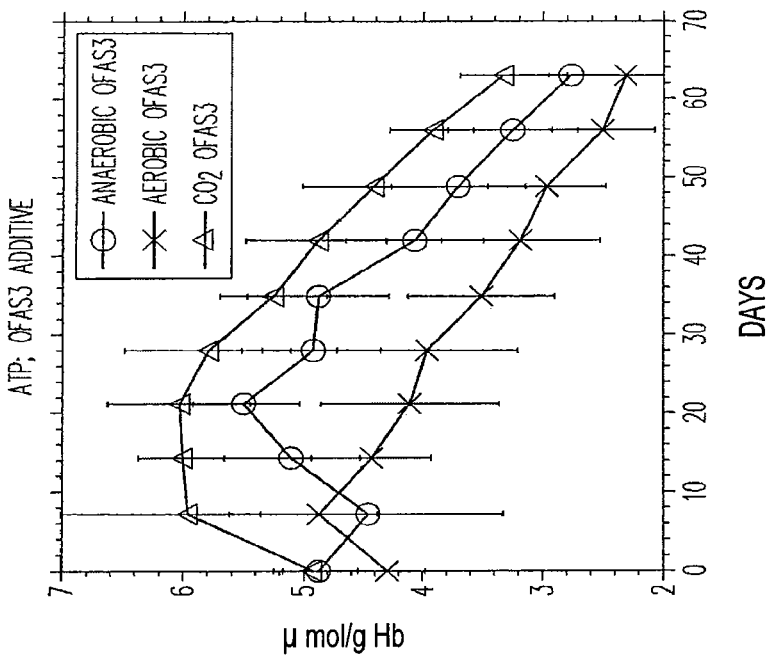

FIG. 12c: ATP levels during storage with OFAS3. Highest ATP levels were achieved with OFAS3 RBC when O$_2$ only was depleted. For O$_2$/CO$_2$ depletion, intermediate levels of ATP were observed compared to the control while very high DPG levels were attained during first 2.5 weeks. Very high levels of ATP may suggest higher rate of 24-hour post transfusion recovery. Therefore, extent of carbon dioxide and oxygen depletion levels may be adjusted to meet the specific requirement of the recipient. DPG levels can be maintained very high (at the expense of ATP) for purposes of meeting acute oxygen demand of recipient. Conversely, very high ATP levels may allow higher 24-hour recovery rate (lower fraction of non-viable RBC upon transfusion) thereby reducing the quantity of blood needed to be transfused (up to 25% of RBC are non-viable). More importantly, this would benefit chronically transfused patients who may not demand highest oxygen transport efficiency immediately after transfusion (DPG level recovers in body after 8-48 hours) who suffers from toxic iron overloading caused by non-viable RBCs.

FIG. 12d: ATP levels during storage with AS3. Highest ATP levels were achieved with AS3 RBC when O$_2$ only was depleted. No significant differences in ATP levels where observed with control and O$_2$ depletion alone.

Figure 12F:
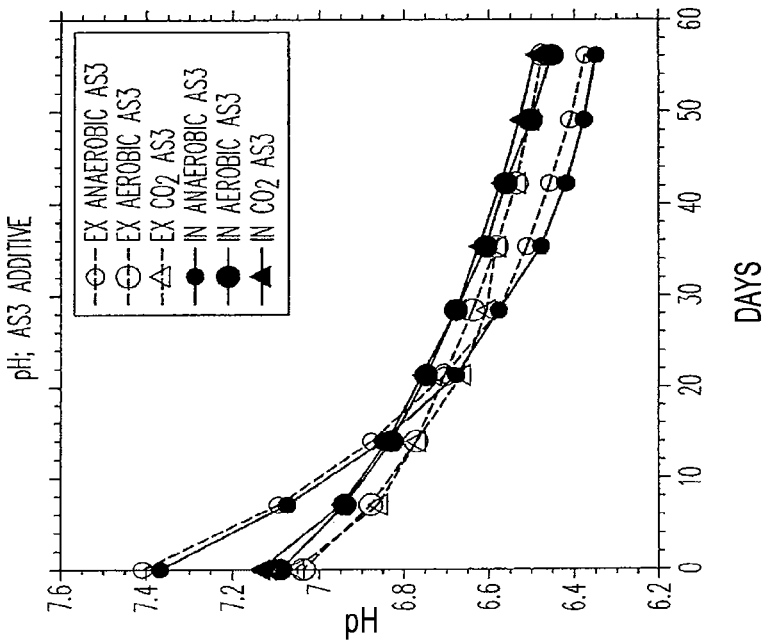
Figure 12E:
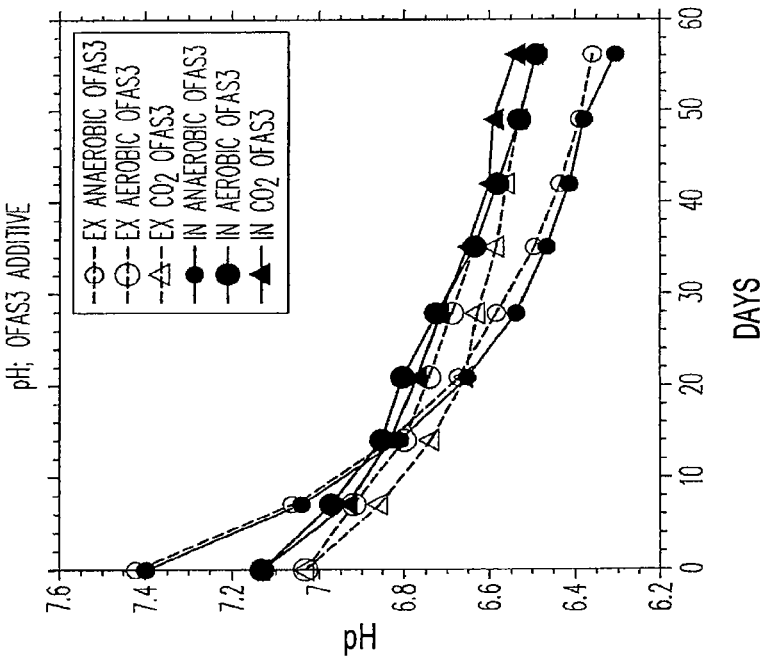

FIGS. 12e and 12f: pH of RBC cytosol (in) and suspending medium (ex). Immediately after gas exchange (day 0), significant rise in pH (in and ex) was observed only when CO$_2$ was depleted together with O$_2$. Rapid rates of pH decline observed with CO$_2$/O$_2$ depleted samples were caused by higher rates of lactate production (FIGS. 12g and 12h).

Figures 12G, 12H:
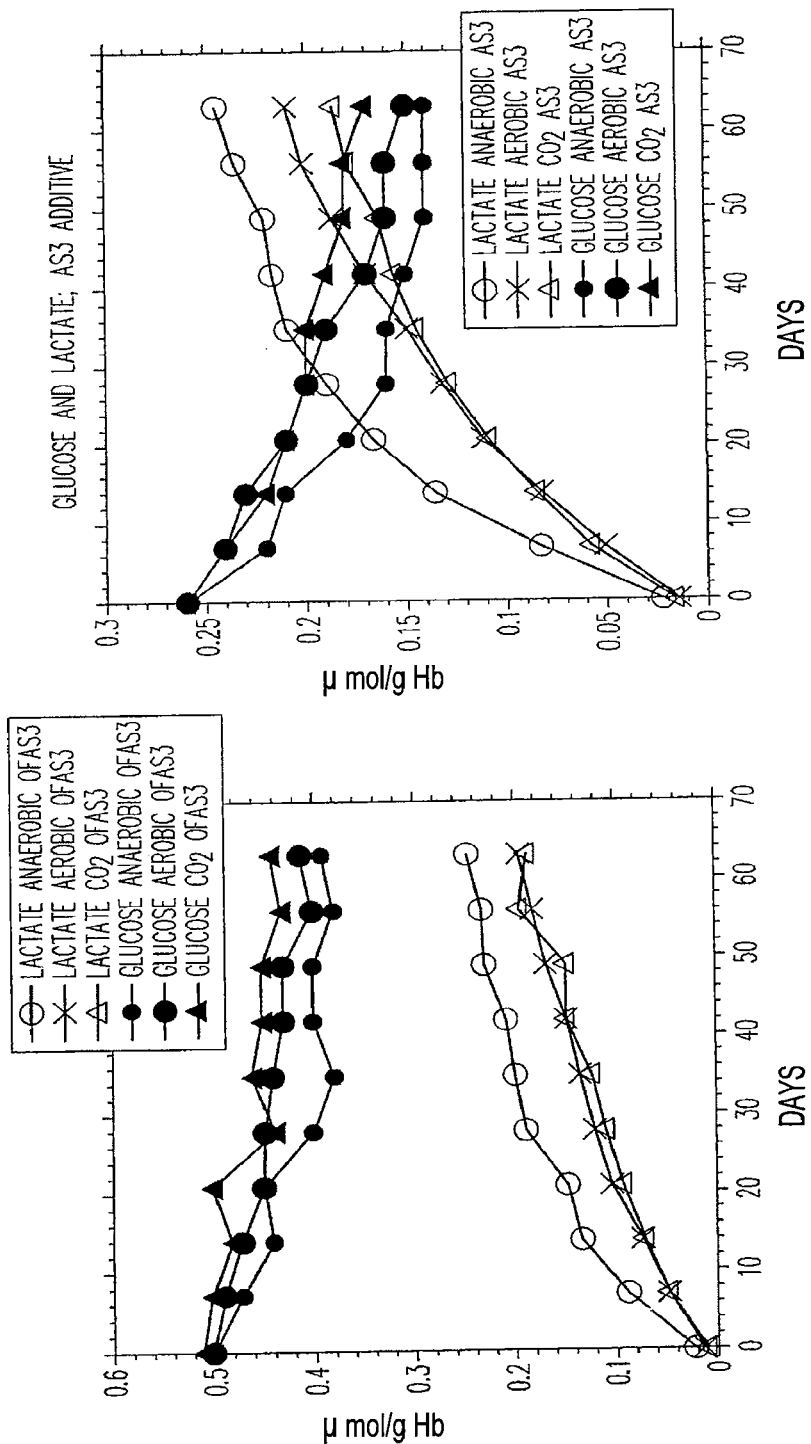

FIGS. 12g and 12h: Normalized (to hemoglobin) glucose and lactate levels during storage with OFAS3 and AS3. Higher rates of glucose depletion and lactate productions correspond to high DPG levels observed in panels A and B. Legends for symbols/lines are same for both panels. OFAS3 additive contains similar glucose concentration with ×2 volume resulting in higher normalized glucose levels.

FIGS. 12a and 12c taken together, suggest that extent of increases (compared to control) of ATP and DPG levels may be adjusted by controlling level of CO$_2$ depletion, when O$_2$ is depleted. Higher glucose utilization and lactate production were observed with enhanced DPG production (FIG. 12g). This may be also effective with AS3 additive, since similar trend in glucose utilization and lactate production were observed (FIG. 12h).

Figure 13:
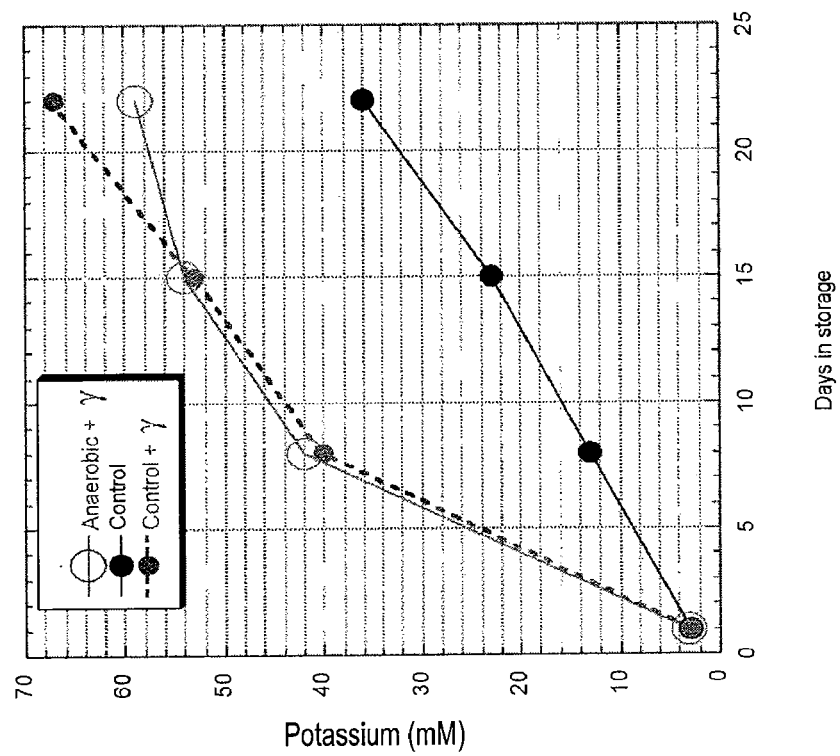
FIG. 13 illustrates an effect of gamma-irradiation on K+ leak rates from RBC (as measured by free K+ concentrations in RBC suspending media after storage).

FIG. 13 shows a graph comparing the effect of gamma irradiation on aerobic and anaerobic RBC. FIG. 13 shows an control unit, RBC that are aerobic and not gamma-irradiated (Unit A, black filled solid line), aerobic RBC that are gamma-irradiated (Unit B; control plus gamma irradiation indicated by a filled circle with dotted line) and an anaerobically depleted RBC unit that has been gamma-irradiated (Unit C; Anaerobic+γ, open circle and solid line). Unit B and Unit C are irradiated and Unit A is non-irradiated and aerobic RBC. The constituent of the blood that is being measured is potassium. The amount of leakage of potassium (K+) from RBC that is measured in the storage media is an indicator of health of the RBC. Therefore, in the context of the present application, a greater level of concentration of potassium in RBC storage media, is indicative of a greater level of RBC damage relative to a lower level of concentration of potassium in RBC storage media.

FIG. 13 indicates that gamma irradiation induced a high rate of K+leakage during the first week for Unit B and Unit C. K+ leakage rates after days eight and fifteen, were similar for all units. Significantly, the difference between K+ leakage between Unit B and Unit C increases beyond the twenty-second day of storage. The results indicate that this trend could exist for several more days. Accordingly, the use of anaerobic depletion and gamma irradiation may permit the extension of current FDA storage limit of twenty-eight days for anaerobically depleted and gamma irradiated blood prepared after component separation.

Irradiating RBC for immuno-compromised individuals is a necessity. The present results show that irradiated RBC that were also oxygen depleted did not increase K+ leakage rates, an indicator of RBC damage. The benefits of oxygen depleted RBC including increased levels of ATP and DPG-2,3 are not negatively impacted by the irradiation.

In graph above, four ABO Rh identical units (in AS3 additive, leukoreduced; standard RBC concentrate obtained from American Red Cross) are pooled. The three units were used for above-graphed experiment from the pooled unit after it was sub-divided into 4 fractions within 24 hours of blood collection and stored at 1-6° C.

Although the present disclosure describes in detail certain embodiments, it is understood that variations and modifications known to those skilled in the art that are within the disclosure. Accordingly, the present disclosure is intended to encompass all such alternatives, modifications and variations that are within the scope of the disclosure as set forth in the disclosure.

What is claimed is:

1. A composition comprising gamma-irradiated, oxygen and carbon dioxide depleted red blood cells without added L-carnitine or an alkanoyl derivative, wherein said gamma-irradiated, oxygen and carbon dioxide depleted red blood cells are prepared by depleting the oxygen saturation of hemoglobin (SO$_2$) to less than 20% and depleting the carbon dioxide partial pressure (pCO$_2$) to less than 10 millimeter of mercury (mmHg), storing oxygen and carbon dioxide depleted red blood cells for a period of time, and then gamma-irradiating the stored oxygen and carbon dioxide depleted red blood cells to form said gamma-irradiated, oxygen and carbon dioxide depleted red blood cells, wherein said gamma-irradiated oxygen and carbon dioxide depleted red blood cells exhibit reduced potassium leakage compared to red blood cells gamma-irradiated after having been conventionally stored for a period of at least 22 days.

2. The composition of claim 1, wherein said gamma-irradiated oxygen and carbon dioxide depleted red blood cells comprise less than 5% oxygen saturation of hemoglobin ($SO_2$).

3. The composition of claim 2, wherein said gamma-irradiated oxygen and carbon dioxide depleted red blood cells comprise less than 3% oxygen saturation of hemoglobin ($SO_2$).

4. The composition of claim 1, wherein said gamma-irradiated oxygen and carbon dioxide depleted red blood cells comprise less than 5 mmHg $pCO_2$.

5. The composition of claim 1, wherein said gamma-irradiated oxygen and carbon dioxide depleted red blood cells comprise less than 1 mmHg $pCO_2$.

6. The composition of claim 1, wherein said composition comprises reduced lesions compared to a composition comprising red blood cells having been conventionally stored for an equivalent period of time prior to being gamma-irradiated.

7. The composition of claim 1, wherein said composition comprises reduced oxidative damage compared to a composition comprising red blood cells having been conventionally stored for an equivalent period of time prior to being gamma-irradiated.

8. The composition of claim 1, wherein said gamma-irradiated oxygen and carbon dioxide depleted red blood cells comprise reduced irradiation damage compared to red blood cells having been conventionally stored for an equivalent period of time prior to being gamma-irradiated.

9. The composition of claim 1, wherein said gamma-irradiated oxygen and carbon dioxide depleted red blood cells comprise increased deformability compared to red blood cells having been conventionally stored for an equivalent period of time prior to being gamma-irradiated.

10. The composition of claim 1, wherein said gamma-irradiated oxygen and carbon dioxide depleted red blood cells comprise reduced hemolysis compared to red blood cells having been conventionally stored for an equivalent period of time prior to being gamma-irradiated.

11. The composition of claim 1, wherein said gamma-irradiated oxygen and carbon dioxide depleted red blood cells exhibit improved post-transfusion recovery compared to red blood cells having been conventionally stored for an equivalent period of time prior to being gamma-irradiated.

12. The composition of claim 11, wherein said improved post-transfusion recovery is after 6 weeks of storage.

13. The composition of claim 1, wherein said composition further comprises an additive solution selected from the group consisting of additive solution 3 (AS-3) and oxygen free additive solution 3 (OFAS3).

14. The composition of claim 1, wherein said composition is stored within a storage vessel substantially impermeable to oxygen or both oxygen and carbon dioxide.

15. The composition of claim 14, wherein said storage vessel comprises an inner layer compatible with blood and an outer layer substantially impermeable to oxygen or both oxygen and carbon dioxide.

16. The composition of claim 14, wherein said storage vessel can be gamma-irradiated.

17. The composition of claim 1, wherein said oxygen and carbon dioxide depleted red blood cells are depleted of oxygen and carbon dioxide by an oxygen and carbon dioxide depletion device comprising gas-permeable films adapted to receiving and conveying red blood cells and an amount of an oxygen scavenger or both oxygen and a carbon dioxide scavenger.

18. The composition of claim 1, wherein said oxygen and carbon dioxide depleted red blood cells are stored at a temperature from between 1° C. and 6° C.

* * * * *